United States Patent
Nakagawa et al.

(10) Patent No.: US 6,818,631 B1
(45) Date of Patent: Nov. 16, 2004

(54) FUNGICIDAL PYRIMIDINE DERIVATIVES

(75) Inventors: Yuki Nakagawa, Gainesville, FL (US); Sergey Bobrov, Gainesville, FL (US); Charles R. Semer, IV, Gainesville, FL (US); Thomas A. Kucharek, Gainesville, FL (US); Masahiro Haramoto, Kanagawa (JP)

(73) Assignee: Nippon Soda Co. Ltd., Tokyo (JP)

( * ) Notice: Subject to any disclaimer, the term of this patent is extended or adjusted under 35 U.S.C. 154(b) by 0 days.

(21) Appl. No.: 10/642,552

(22) Filed: Aug. 15, 2003

(51) Int. Cl.$^7$ .................. C07D 401/14; C07D 403/04; A01N 43/54
(52) U.S. Cl. ............. 514/63; 514/256; 514/274; 544/229; 544/315; 544/333; 544/334
(58) Field of Search .............. 544/229, 315, 544/333, 334; 514/63, 256, 274

(56) References Cited

U.S. PATENT DOCUMENTS

| 3,149,109 A | 9/1964 | Rorig et al. |
| 4,474,599 A | 10/1984 | Rogers et al. |

FOREIGN PATENT DOCUMENTS

| DE | 197 28 996 A1 | 7/1997 |
| EP | 0 337 943 A2 | 4/1989 |
| EP | 0407899 A2 * | 1/1991 |
| WO | WO 9408975 A1 | 4/1994 |
| WO | WO 9633972 A1 | 10/1996 |
| WO | WO 2002047690 A | 6/2002 |
| WO | WO 2002067684 A | 9/2002 |
| WO | WO 2003000659 A | 1/2003 |

* cited by examiner

Primary Examiner—Deepak Rao
(74) Attorney, Agent, or Firm—Dennis G. LaPointe; Mason Law, P.L.

(57) ABSTRACT

Fungicidal pyrimidine derivatives and the use as a fungicide of the compounds of formula (1):

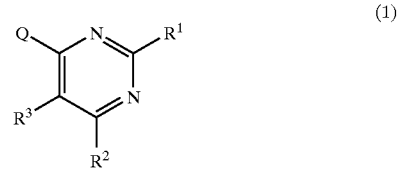

wherein $R^1$ is H, $C_1$–$C_6$alkyl, $C_2$–$C_6$alkenyl, $C_2$–$C_6$alkynyl $C_3$–$C_6$cycloalkyl, $C_1$–$C_6$alkoxy, $C_3$–$C_6$cycloalkoxy, $C_1$–$C_6$alylthio, $C_1$–$C_6$alkylsulfinyl, $C_1$–$C_6$alkylsulfonyl, phenyl, pyridinyl or azolyl groups, (being optionally substituted by one or more substituents); or $N(R^4)C(O)R^5$, $R^2$ is polyfluoroalkyl, $R^3$ is fluorine, chlorine, bromine or iodine; ethenyl or ethynyl (being optionally substituted by one or more of halogen), $R^4$ and $R^5$ are, independently, H, $C_1$–$C_6$alkyl, $C_2$–$C_6$alkenyl or $C_2$–$C_6$alkynyl groups, (being optionally substituted by one or more of halogen or cyano); or $R^4$ and $R^5$ can join together to form a 5 or 6-membered ring, Q is a heteroaromatic ring selected from the following ring system; imidazol-1-yl, pyrazol-1-yl, 1,2,3-triazol-1-yl, 1,2,3-triazol-2-yl, 1,2,4-triazol-1-yl, 1,2,4-triazol-1-yl, benzimidazol-1-yl or tetrazol-5-yl groups, (being optionally substituted by one or more of substituents).

2 Claims, No Drawings

FUNGICIDAL PYRIMIDINE DERIVATIVES

BACKGROUND OF THE INVENTION

1. Field of the Invention

The present invention relates to novel pyrimidine derivatives, which have fungicidal activity. The preparation and use, in agriculture and horticulture, of agrochemical compositions containing these novel fungicidal pyrimidines are also disclosed.

2. Description of the Related Art

It is known in the art that certain pyrimidine derivatives such as those disclosed in PCT application WO 2003-000659 have fungicidal and insecticidal properties, WO 2002-067694 have pesticidal properties, EP 337943 have herbicidal and plant growth regulatory properties, U.S. Pat. No. 4,474,599 have herbicidal properties and in the art that PCT application WO 94-08975 have herbicidal and fungicidal properties. In the arts that WO 2002-047690, WO 99-02503, WO 96-33972 and U.S. Pat. No. 3,149,109 also have description about heteroaromatic substituted pyrimidine derivatives.

SUMMARY OF THE INVENTION

In accordance with the present invention, pyrimidine derivatives are provided having the formula (1):

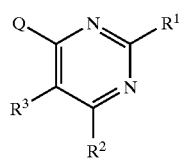

(1)

Wherein $R^1$ is H, $C_1$–$C_6$alkyl (being optionally substituted by one or more of halogen), $C_2$–$C_6$alkenyl (being optionally substituted by one or more of halogen), $C_2$–$C_6$alkynyl (being optionally substituted by one or more of halogen or trialkylsilyl), $C_1$–$C_6$alkoxy (being optionally substituted by one or more of halogen), $C_2$–$C_6$alkenyloxy (being optionally substituted by one or more of halogen), $C_2$–$C_6$alkynyloxy (being optionally substituted by one or more of halogen), $C_1$–$C_6$alkylthio (being optionally substituted by one or more of halogen), $C_1$–$C_6$alkylsulfinyl (being optionally substituted by one or more of halogen), $C_1$–$C_6$alkylsulfonyl (being optionally substituted by one or more of halogen), phenyl (being optionally substituted by one or more of halogen, alkyl, haloalkyl or alkoxy), pyridin-2-yl (being optionally substituted by one or more of halogen, alkyl, haloalkyl or phenyl), pyridin-3-yl (being optionally substituted by one or more of halogen, alkyl, haloalkyl or phenyl), pyridinyl (being optionally substituted by one or more of halogen, alkyl, haloalkyl or phenyl), imidazol-1-yl (being optionally substituted by one or more of halogen, alkyl or alkoxyl pyrazol-1-yl (being optionally substituted by one or more of halogen, alkyl or alkoxy) or $N(R^4)C(O)R^5$, $R^2$ is halo$C_1$–$C_6$alkyl, $R^3$ is halogen, $C_2$–$C_6$alkenyl or $C_2$–$C_6$alkynyl groups, (being optionally substituted by one or more of halogen), $R^4$ and $R^5$ are, independently, H, $C_1$–$C_6$alkyl (being optionally substituted by one or more of halogen or cyano); or $R^4$ and $R^5$ can join together to form a 5 or 6-membered ring, Q is a heteroaromatic ring selected from the following ring system; imidazol-1-yl, pyrazol-1-yl, 1,2,3-triazol-1-yl, 1,2,3-triazol-2-yl, 1,2,4-triazol-1-yl, 1,2,4-triazol-4-yl, benzimidazol-1-yl or tetrazol-5-yl groups (being optionally substituted by one or more of halogen, cyano, hydroxy, mercapto, alkyl, haloalkyl, alkoxy, alkoxycarbonyl, amino, alkylamino, haloalkoxy, alkylthio or aralkylthio).

The present invention is directed to agrochemical compositions comprising as an active ingredient at least one of the novel pyrimidine derivatives of the present invention, as well as to the use of these active ingredients or compositions for plant disease control and in particular as fungicides useful in agriculture and horticulture.

For a better understanding of the present invention, reference is made to the following description and its scope will be pointed out in the appended claims.

DETAILED DESCRIPTION OF THE INVENTION

For purposes of the present invention the general terms used hereinabove and hereinbelow have the following meanings, unless otherwise defined:

Alkyl groups are, in accordance with the number of carbon atoms, straight-chain or branched and will typically be methyl, ethyl, n-propyl, isopropyl, n-butyl, sec-butyl, isobutyl, tert-butyl, n-amyl, tert-amyl, 1-hexyl or 3-hexyl.

Halogen and halo substituents will be understood generally as meaning fluoro, chloro, bromo, iodo, Haloalkyl can contain identical or different halogenatoms, typically fluoromethyl, difluoromethyl, difluorochloromethyl, trifluoromethyl, chloromethyl, trichloromethyl.

Alkoxy is typically methoxy, ethoxy, propyloxy, isopropyloxy, n-butyloxy, isobutyloxy, sec-butyloxy and tert-butyloxy.

Alkenyl and alkynyl groups preferably contain from 2 to 6, more preferably from 2 to 4, carbon atoms. They can be in the form of straight or branched chains, and, where appropriate, the alkenyl groups can be of either (E) or (Z)-configuration. Examples are vinyl, ethynyl, propynyl.

The present invention provides the use as fungicides of pyrimidine derivatives having the following formula (1):

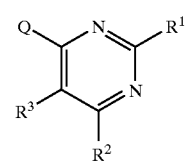

(1)

Wherein $R^1$ is H, $C_1$–$C_6$alkyl (being optionally substituted by one or more of halogen), $C_2$–$C_6$alkenyl (being optionally substituted by one or more of halogen), $C_2$–$C_6$alkynyl (being optionally substituted by one or more of halogen or trialkylsilyl), $C_1$–$C_6$alkoxy (being optionally substituted by one or more of halogen), $C_2$–$C_6$alkenyloxy (being optionally substituted by one or more of halogen), $C_2$–$C_6$alkynyloxy (being optionally substituted by one or more of halogen), $C_1$–$C_6$alkylthio (being optionally substituted by one or more of halogen), $C_1$–$C_6$alkylsulfinyl (being optionally substituted by one or more of halogen), $C_1$–$C_6$alkylsulfonyl (being optionally substituted by one or more of halogen), phenyl (being optionally substituted by one or more of halogen, alkyl, haloalkyl or alkoxy), pyridin-2-yl (being optionally substituted by one or more of halogen, alkyl, haloalkyl or phenyl), pyridin-3-yl (being optionally substituted by one or more of halogen, alkyl, haloalkyl or phenyl), pyridin-4-yl (being optionally substituted by one or more of halogen, alkyl, haloalkyl or phenyl), imidazol-1-yl (being optionally substituted by one or more of halogen, alkyl or alkoxy), pyrazol-1-yl (being optionally substituted by one or more of halogen, alkyl or alkoxy) or $N(R^4)C(O)R^5$, $R^2$ is haloC$_1$–C$_6$akyl, $R^3$ is halogen, C$_2$–C$_6$alkenyl or C$_2$–C$_6$alkynyl groups, (being optionally substituted by one or more of halogen), $R^4$ and $R^5$ are, independently, H, C$_1$–C$_6$alkyl (being optionally substituted by one or more of halogen or cyano); or $R^4$ and $R^3$ can join together to form a 5 or 6membered ring, Q is a heteroaomatic ring selected from the following ring system; imidazol-1-yl, pyrazol-1-yl, 1,2,3-triazol-1-yl, 1,2,3-triazol-2-yl, 1,2,4-triazol-1-yl, 1,2,4-triazol-4-yl, benzimidazol-1-yl or tetrazol-5-yl groups (being optionally substituted by one or more of halogen, cyano, hydroxy, mercapto, alkyl, haloalkyl, alkoxy, alkoxycarbonyl, amino, alkylamino, haloalkoxy, alkylthio or aralkylthio).

Examples of specific compounds of formula (1) which are of use as fungicides include the compounds listed in Table 1.

The pyrimidine derivative represented by the formula (1) in the invention can be prepared by the following process.

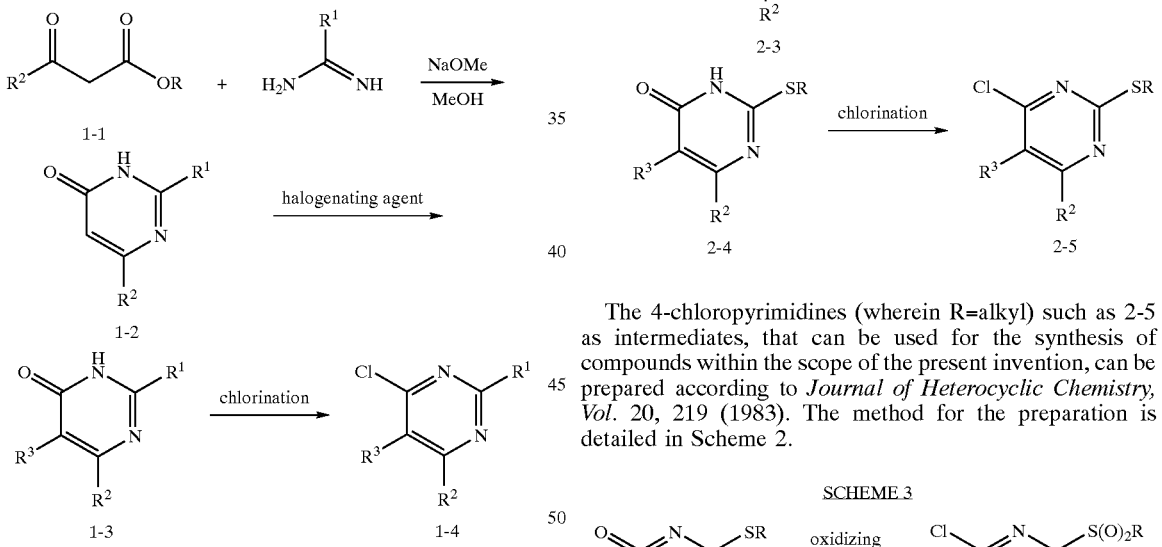

The preparation of 5-halogenated 4chloropyrimidines (wherein $R^1$=H, alkyl phenyl, pyridine-2-yl, pyridine-3-yl or pyridine-4-yl) such as 14 as intermediates that can be used for the synthesis of compounds within the scope of the present invention is detailed in Scheme 1. Pyrimidinones of structure 1-2 can be synthesized by condensation of a β-keto-ester with amidine (or amidine salt) in a suitable solvent such as methanol, ethanol, isopropanol or the like in the presence of a base such as sodium or potassium alkoxide. The pyrimidinones 1-2 thus obtained can be halogenated by treatment with a suitable halogenating agent such as bromine, chlorine, iodine monochloride, N-bromosuccinimide, N-chlorosuccinimide or N-iodosuccinimide in a suitable solvent such as dichloromethane, chloroform, carbon tetrachloride, acetonitrile or N,N-dimethylformamide to give a halogenated pyrimidinone at 5-position of structure 1-3 (wherein $R^3$=Cl, Br, I). The pyrimidinone can be chlorinated by treatment with phosphoryl chloride, phosphorous pentachloride, phosphorous trichloride or mixtures thereof or with chloromethylenedimethylammonium chloride added separately of prepared in situ by treatment of N,N-dimethylformamide with thionyl chloride, phosgene or the like in dichloromethane, chloroform, tetrahydrofuran, dioxane, ether or other suitable solvent to give a 4-chloropyrimidine of structure 1-4.

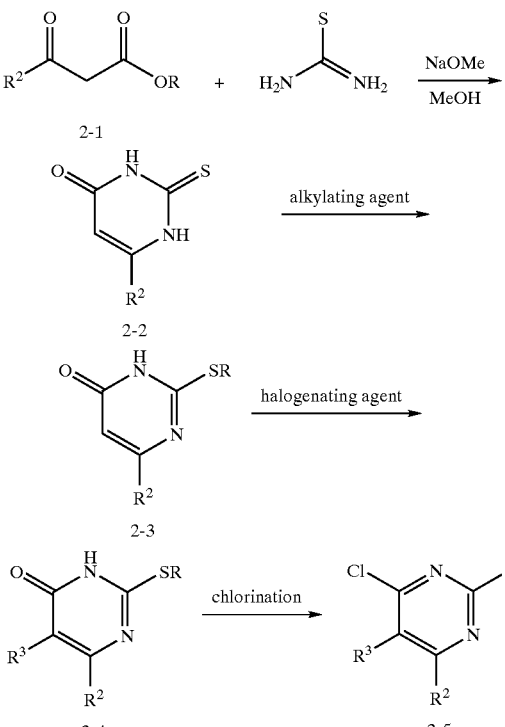

The 4-chloropyrimidines (wherein R=alkyl) such as 2-5 as intermediates, that can be used for the synthesis of compounds within the scope of the present invention, can be prepared according to *Journal of Heterocyclic Chemistry, Vol.* 20, 219 (1983). The method for the preparation is detailed in Scheme 2.

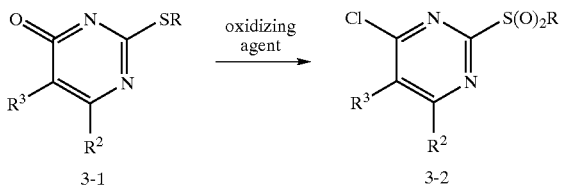

The preparation of 2-alkylsulfonyl-4-chloropyrimidines such as 3-2 as intermediates that can be used for the synthesis of compounds within the scope of the present invention is detailed in Scheme 3. A 2-alkylthio-4-chloropyrimidine 3-1 is treated with oxidizing agent such as hydrogen peroxide or m-chloroperbenzoic acid in a suitable solvent such as dichloromethane, chloroform, acetic acid or the like to give a 2-alkylsulfonyl-4-chloropyrimidine of structure 3-2.

SCHEME 4

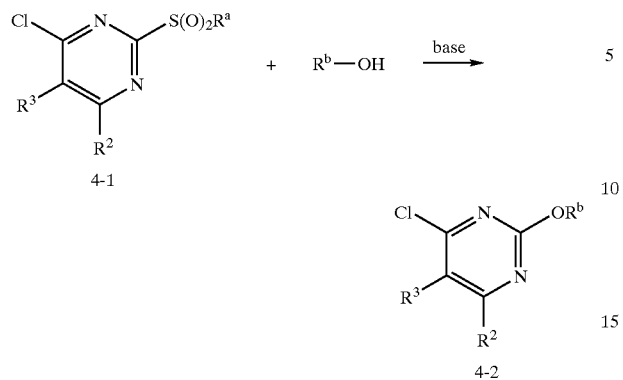

The preparation of 2-alkoxy-4-chloropyrimidines such as 4-2 as intermediates that can be used for the synthesis of compounds within the scope of the present invention is detailed in Scheme 4. A 2-alkylsulfonyl-4-chloropyrimidine 4-1 is treated with an alcohol in the presence of a base such as sodium hydride, sodium bis(trimethylsilyl)amide, potassium tert-butoxide or the like to give a 2-alkoxy-4-chloropyrimidine of structure 4-2.

SCHEME 5

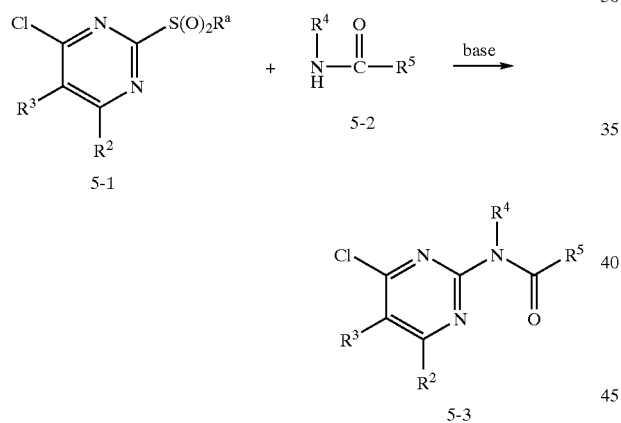

The preparation of 2-alkylcarbonylamino-4-chloropyrimidines such as 5-3 as intermediates that can be used for the synthesis of compounds within the scope of the present invention is detailed in Scheme 5. A 2-alkysulfonyl-4-chloropyrimidine 5-1 is treated with a carboxylic amide 5-2 in the presence of a base such as sodium hydride, sodium bis(trimethylsilyl)amide, potassium tert-butoxide or the like to give a 2-alkoxy-4-chloropyrimidine of structure 5-3.

SCHEME 6

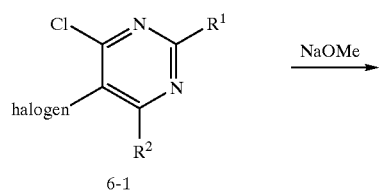

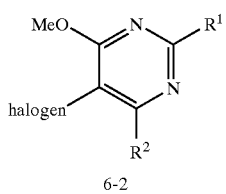

The preparation of 5-halogeno-4-methoxypyrimidines such as 6-2 as intermediates that can be used for the synthesis of compounds within the scope of the present invention is detailed in Scheme 6. A 4-chloropyrimidine of structure 6-1 is treated with sodium methoxide in a suitable solvent such as methanol, tetrahydrofuran or the like to give a 4methoxypyrimidine of structure 6-2.

SCHEME 7

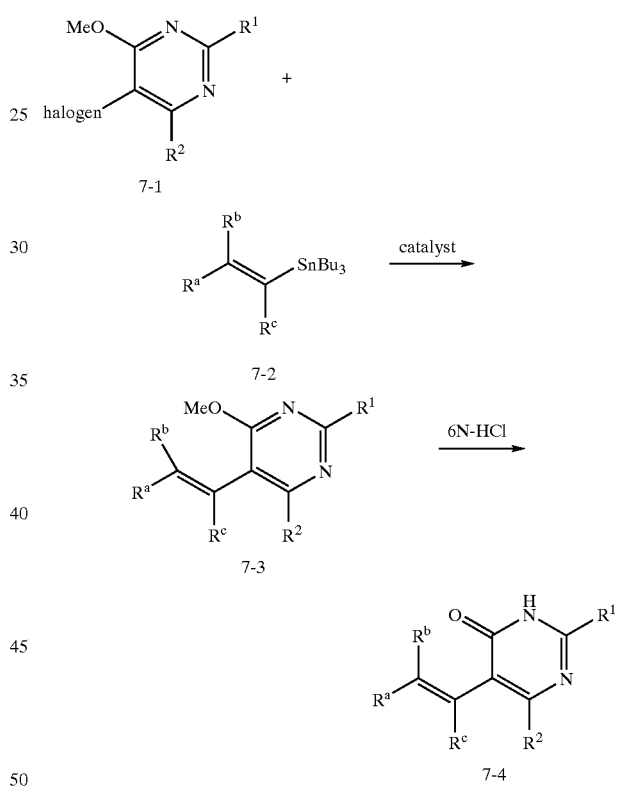

The preparation of 5-alkenylpyrimidinones such as 7-4 as intermediates that can be used for the synthesis of compounds within the scope of the present invention is detailed in Scheme 7. A 5-halogenooxypyrimidine 7-1 (halogen=Br or I) is treated with alkenyltributyltin 7-2 in the presence of a catalyst such as tetrakis(triphenylphosphine)palladium(0), dichlorobis(triphenylphosphine)palladium(II), triphenylarsinepalladium(0) or the like in a suitable solvent such as N,N-dimethylformamide, acetonitrlile, dioxane, tetrahydrofuran, toluene or other suitable solvent to give a 5-alkeny-4-methoxypyrimidine of structure 7-3. The 5-alkenyl-4-methoxypyrimidine thus obtained is treated with 6N-HCl under reflux to give a 5-alkenylpyrimidinone of structure 7-4.

SCHEME 8

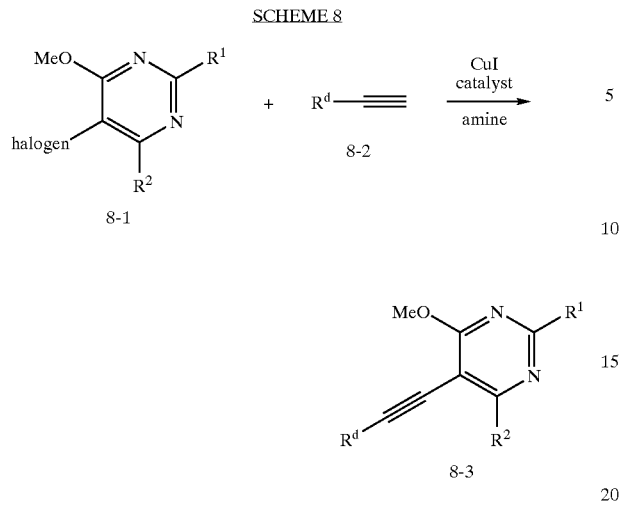

The preparation of 5-alkynyl-4-methoxypyrimidines such as 8-3 as intermediates that can be used for the synthesis of compounds within the scope of the present invention is detailed in Scheme 8. A 5-halogeno-4-methoxypyrimidine 8-1 (halogen=Br or I) is treated with alkyne 8-2 in the presence of amine such as triethylamine, n-propylamine, N,N-diisopropylethylamine or the like, copper(I) iodide and catalyst such as tetrakis(triphenylphosphine)palladium(0), dichlorobis(triphenylphosphine)palladium(II) or the like in a suitable solvent such as N,N-dimethylformamide, acetonitrlile, dioxane, tetrahydrofuran, toluene or other suitable solvent to give a 5-alkynyl-4-methoxypyrimidine of structure 8-3.

SCHEME 9

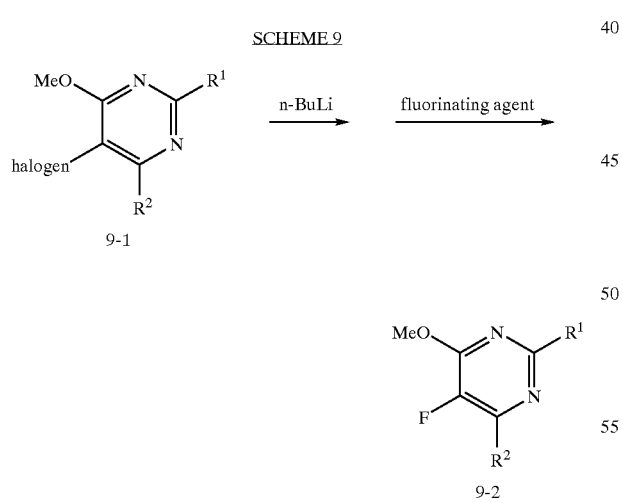

The preparation of 5-fluoro-4-methoxypyrimidines such as 9-2 as intermediates that can be used for the synthesis of compounds within the scope of the present invention is detailed in Scheme 9. A 5-halogeno-4-methoxypyrimidine 9-1 (halogen=Br or I) is treated with n-butyl lithium under dry ice cooling, then with fluorinating agent such as N-fluorobenzenesulfonimide, 1-fluoropyridinium tetrafluoroborate or the like in a suitable solvent such as tetrahydrofurwan, ether or other suitable solvent to give a 5-fluoro-4-methoxypyrimidine of structure 9-2.

SCHEME 10

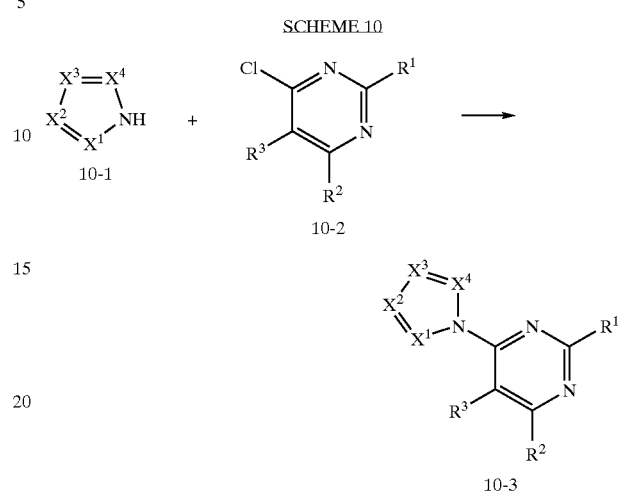

The preparation of some 4-azolylpyrimidines such as 10-3 within the scope of the present invention is detailed in Scheme 10. An azole 10-1 is condensed with a 4-chloropyrimidine 10-2 in a suitable solvent such as dimethysulfoxide, acetonitrile, tetrahydrofuran, toluene, isopropanol or the like in the presence or absence of a base such as sodium hydride, sodium hydroxide, potassium carbonate, 1,8-diazabicyclo-([5,4,0]-undec-7-ene, N,N-diisopropylethylamine or the like at or above room temperature to give a 4-azolylpyrimidine of structure 10-3.

SCHEME 11

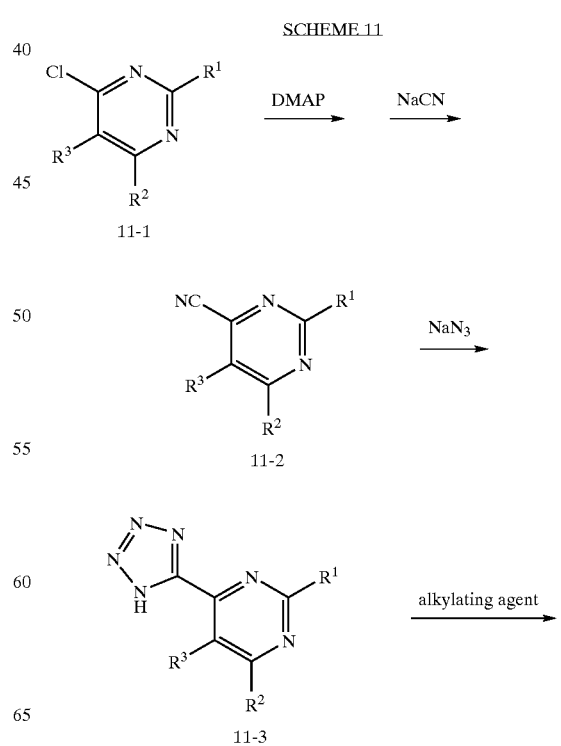

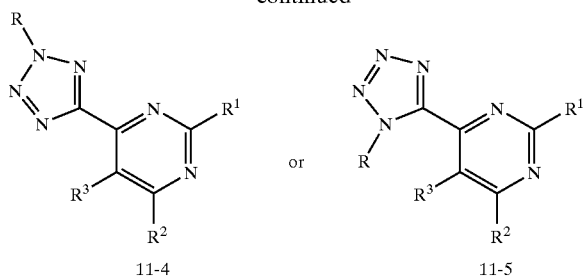

11-4 or 11-5

The preparation of some 4-tetrazolyl pyrimidines such as 11-3, 11-4 and 11-5 within the scope of the present invention is detailed in Scheme 11. A 4-chloropyrimidine 11-1 is treated with cyanating agent such as sodium or potassium cyanide in a suitable solvent such as water, isopropanol, acetonitrile, propionitrile, tetrahydrofuran, N,N-dimethylformamide, dimethylsulfoxide or mixture thereof, or other suitable solvent to give a 4-cyanopyrimidine of structure 11-2. The 4-chloropyrimidine 11-1 can first be activated by addition of 4-(dimethylamino)pyridine prior to be added cyanating agent. The 4-cyanopyrimidine thus obtained is treated with sodium azide in a suitable solvent such as water, isopropanol, acetonitrile, propionitrile, tetrahydrofuran, N,N-dimethylformamide, dimethylsulfoxide or mixture thereof or other suitable solvent to give 4-tetrazolylpyrimidine of structure 11-3. This reaction can be accelerated by adding zinc bromide or other zinc halides. The 4-tetrazolylpyrimidine thus obtained can be methylated by treatment with trimethylsilyldiazomethane or alkylated by treatment with a suitable alkylating agent such as dimethyl sulfate, diethyl sulfate, methyl iodide, isopropyl iodide or the like in the presence or absence of an inorganic base such as sodium hydroxide, potassium hydroxide, sodium hydride and potassium carbonate or organic base such as triethylamine and pyridine to give a alkylated tetrazolylpyrimidine of structure 11-4 or 11-5.

The compounds of the present invention can show excellent fungicidal activity against wide varieties of fungi, and therefore, the compounds can be useful for plant disease control in the farming of agricultural and horticultural crops including ornamental flowers, turf and forage crops.

The examples for the plant diseases might to be controlled with the compounds of the present invention are given in the following.

| Paddy rice | |
|---|---|
| Blast | (*Pyricularia oryzae*) |
| Sheath blight | (*Rhizoctonia solani*) |
| Bakanae disease | (*Gibberella fujikuroi*) |
| Helminthosporium leaf spot | (*Cochliobolus miyabeanus*) |
| Barley | |
| Loose smut | (*Ustilago muda*) |
| Wheat | |
| Scab | (*Gibberella zeae*) |
| Leaf rust | (*Puccinia recondita*) |
| Eye spot | (*Pseudocercosporella herpotrichoides*) |
| Glume blotch | (*Leptosphaeria nodorum*) |
| Powdery mildew | (*Erysiphe graminis f sp. tritici*) |
| Fusarium snow blight | (*Micronectriella nivalis*) |
| Potato | |
| Late blight | (*Phytophthora infestans*) |
| Gray mold | (*Botrytis cinerea*) |
| Ground nut | |
| Leaf spot | (*Mycosphaerella aradius*) |
| Sugar beat | |
| Cercospora leaf spot | (*Cercospora beticola*) |
| Soybean | |
| Gray mold | (*Botrytis cinerea*) |
| Kidney beans | |
| Gray mold | (*Botrytis cinerea*) |
| Cucumber | |
| Powdery mildew | (*Sphaerotheca fuliginea*) |
| Sclerotinia rot | (*Sclerotinia sclerotiorum*) |
| Gray mold | (*Botrytis cinerea*) |
| Downy mildew | (*Pseudoperonospora cubensis*) |
| Tomato | |
| Leaf mold | (*Cladosporium fulvum*) |
| Late blight | (*Phytophthora infestans*) |
| Gray mold | (*Botrytis cinerea*) |
| Egg plant | |
| Black rot | (*Corynespora melongenae*) |
| Onion | |
| Gray mold neck rot | (*Botrytis allii*) |
| Strawberry | |
| Powdery mildew | (*Sphaerotheca humuli*) |
| Gray mold | (*Botrytis cinerea*) |
| Apple | |
| Powdery mildew | (*Podosphaera leucotricha*) |
| Scab | (*Venturia inaequalis*) |
| Blossow blight | (*Monilinia mali*) |
| Persimmon | |
| Anthracnose | (*Gloeosporium kala*) |
| Peach | |
| Brown rot | (*Monilinia fructicola*) |
| Grape | |
| Powdery mildew | (*Uncinula necator*) |
| Downy mildew | (*Plasmopara viticola*) |
| Gray mold | (*Botrytis cinerea*) |
| Pear | |
| Rust | (*Gymnosporangium asiaticum*) |
| Black spot | (*Alternaria kikuchiana*) |
| Tea-plant | |
| Leaf spot | (*Pestalotia theae*) |
| Anthracnose | (*Colletotrichum theae-sinensis*) |
| Orange | |
| Scab | (*Elsinoe fawcetti*) |
| Blue mold | (*Penicillium italicum*) |
| Turf | |
| Sclerotinia snow blight | (*Sclerotinia borealis*) |

In recent years, it is known that various pathogenic fungi have developed their resistance to benzimidazole fungicides and ergosterol biosynthesis inhibitors and that such fungicides have been insufficient in their fungicidal effectiveness. Therefore, it is required to provide new compounds useful as a fungicide which are effective to the resistant-strain of such pathogenic fungi as well. The compounds of the present invention are the ones which can be a fungicide having excellent fungicidal effectiveness not only to the acceptible-strains of pathogenic fungi but also to the resistant-strains of pathogenic fungi to benzinidazole fungicides and ergosterol biosynthesis inhibitors.

The compounds of the present invention can be utilized as an antifouling agent for preventing the adhesion of aqueous organisms to structures, such as the bottom of a ship and fishing nets, in water and sea.

Also, the compounds of the present invention can be contained in paints and fibers and thereby used as an antimicrobial agent for walls, bathtubs, shoes and clothes.

Furthermore, some of the compounds of the present invention can show insecticidal, acaricidal and herbicidal activities.

In the practical application of the compounds of the present invention obtained as described above, the compounds can be used in the state as it is without formulation, or, for the use as agricultural plant protection chemicals, the compounds can be applied in forms of general formulations for agricultural plant protection chemicals, such as wettable powders, granules, powders, emulsifiable concentrates, aqueous solutions, suspensions and flowables. For the additives and carriers to be used in the formulations described above, vegetable powders, such as soybean powder and wheat powder, mineral fine powders, such as diatomaceous earth, apatite, gypsum, talc, bentonite, pyrophyllite and clay, and organic and inorganic compounds, such as sodium benzoate, urea and Glauber's salt, can be used, when the compounds are formulated into solid formulations. Whereas, when the compounds are formulated into liquid formulations, petroleum fractions, such as kerosine, xylene and solvent naphtha, cyclohexane, cyclohexanone, dimethylformamide, dimethyl sulfoxide, alcohols, acetone, trichloro ethylene, methylisobutyl ketone, mineral oils, vegetable oils and water, can be used as the solvent. In these formulations, surface active agents may be added to the formulations in order to make the formulations homogeneous and stable, if appropriate.

The content of the compound of the present invention as the active principle in the formulations is preferably in a range of from 5 to 70%.

The wettable powders, the emulsifiable concentrates and the flowable formulation comprising the compound of the present invention prepared as described above can be applied in a form prepared by diluting the formulations with water to the suspension or the emulsion at a desired concentrations, while the powders and the granules of the said compound can be directly applied to plants without dilution.

The compounds of the present invention can demonstrate sufficient effectiveness on plant diseases independently; however, it is also possible to use the said compound in admixing with 1 or more of other fungicides, insecticides, acaricides or synergists.

The followings are the examples for the fungicides, insecticides, acaricides, nematocides and plant growth regulators, those which are usable in admixing with the compounds of the present invention.

Fungicides
  Copper-Based Fungicides
  Basic copper chloride, basic copper sulfate, etc.
  Sulphur-based Fungicides
  Thiram, maneb, mancozeb, polycarbamate, propineb, ziram, zineb, etc.
  Polyhaloalkylthio Fungicides
  Captan, dichlofluanid, folpet, etc.
  Organochlorine Fungicides
  Chlorothalonil, fthalide, etc.
  Organophosphorous Fungicides
  IBP, EDDP, tolcolofos-methyl, pyrazophos, fosetyl-Al, etc.
  Benzimidazole Fungicides
  Thiophanate-methyl, benomyl, carbendazim, thiabendazole, etc.
  Dicarboxyimide Fungicides
  Oxycarboxine, mepronyl, flutolanil, techlofthalam, trichiamide, pencycuron, etc.
  Acyl Alanine Fungicides
  Metalaxyl, oxadixyl, furalaxyl etc.
  EBI Fungicides
  Triadimefon, triadomenol, bitertanol, microbutanil, hexaconazol, propiconazole, triflumizole, procloraz, peflazoate, fenarimol, pyrifenox, trifolin, flusilazole, etaconazole, diclobutrazol, fluotrimazole, flutriafen, penconazole, diniconazole, cyproconazole, imazalil, tridemorph, fenpropimorph, buthiobate, etc.
  Antibiotics
  Polyoxin, blasticidin-S, kasugamycin, validamycin, streptomycin sulfate, etc.
  Others
  Propamocarb hydrochloride salt, quintozene, hydroxyisoxazole, metasulfocarb, anilazine, isoprothiolane, probenazole, quinomethionate, dithianone, dinocap, dichlomezine, mepaniprim, ferimzone, fluazinam, pyroquilon, tricyclazole, oxolinic acid, dithianone, iminoctazine acetate salt, cymoxanil, pyrrolenitrine, metasulfocarb, diethofensarb, binapacryl, lecithin, sodium hydrogencarbonate, fenaninosulf, dodine, dimnethomorph, fenazine oxide, etc.
Insecticides and Acaricides
  Organophosphorous and Carbamate Insecticides
  Fenthion, fenitrothion, diazinon, chlorpyrifos, ESP, vamidothion, fenthoate, dimethoate, formothion, malathon, trichlorfon, thiometon, phosmet, dichlorvos, acephate, EPBP, methyl parathion, oxydimeton methyl, ethion, salithion, cyanophos, isoxathion, pyridafenthion, phosalon, methydathion, sulprofos, chlorfenvinphos, tetrachlorvinphos, dimethylvinphos, propaphos, isofenphos, ethylthiometon, profenofos, pyraclophos, monocrotophos, azinphos methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, fenoxycarb, cartap, thiocyclam, bensultap, etc.
  Pyrethroid Insecticides
  Permethrin, cypermethrin, deltamethrin, fenvalerate, fenpropathrin, pyrethrin, allethrin, tetramethrin, resmethrin, dimethrin, propathrin, fenothrin, prothrin, fluvalinate, cyfluthrin, cyhalothrin, flucythrinate, ethofenprox, cycloprothrin, tralomethrin, silafluophen, brofenprox, acrinathrin, etc.
  Benzoyl Urea-Based Insecticides and Others:
  Diflubenzuron, chlorfluazuron, hexaflumuron, triflumuron, tetrabenzuron, flufenoxuron, flucycloxuron, buprofezin, pyriproxyfen, methoprene, benzoepin, diaphenthiuron, imidacloprid, fipronil, nicotine sulfate, rotenone, meta-aldehyde, machine oil *Bacillus thuringiensis*, microbial insecticides such as insect-pathogenic viruses, etc.
  Nematocides
  Fenamiphos, phosthiazate, etc.
  Acaricides
  Chlorbenzilate, phenisobromolate, dicofol, amitra BPPS, benzomate, hexythiazox, fenbutatin oxide, polynactin, quinomethionate, CPCBS, tetradifon, avermectin, milbemectin, chlofentezin, cyhexatin, pyridaben, fenpyroxymate, tebufenpyrad, pyrimidifen, fenothiocarb, dienochlor, etc.

Plant Growth Regulators

Gibberellines (Gibberelline $A_3$, Gibberelline $A_4$, Gibberelline $A_7$, etc.), IAA, and NAA.

EXAMPLES

The following examples serve to provide further appreciation of the invention but are not meant in any way to restrict the effective scope of the invention. The structures of isolated novel compounds were confirmed by NMR, Mass, and/or other appropriate analysis.

Example 1

5-Bromo-2-methylthio-6-trifluoromethyl-3H-pyrimidin-4-one

2-Methylthio-4-trifluoromethyl-3H-pyrimidin-4-one (20.0 g). was dissolved in acetonitrile (100 ml) and N-bromosuccinimide (18.7 g) was added at room temperature with stirring. The mixture was refluxed for 5 hr and the solvent was removed under reduced pressure. The precipitates were mixed with water, filtered off and dried. The solid thus obtained was mixed with hot hexane and filtered off to give 5-bromo-2-methylthio-6-trifluoromethyl-3H-pyrimidin-4-one (25.3 g) as colorless needles, mp 215–216° C.

Example 2

5-Iodo-2-isopropylthio-6-trifluoromethyl-3H-pyrimidin-4-one

2-Isopropylthio-6-trifluoromethyl-3H-pyrimidin-4-one (23.3 g) was dissolved in acetonitrile (230 ml) and N-iodosuccinimide (24.2 g) was added at room temperature with stirring. The mixture was refluxed for 2.5 hr and the solvent was removed under reduced pressure. The precipitates were dissolved in ethyl acetate, and then washed with aqueous sodium thiosulfate, water and brine, respectively. The ethyl acetate layer was dried over magnesium sulfite and the solvent was removed under reduced pressure to give 5-iodo-2-isopropylthio-6-trifluoromethyl-3H-pyrimidin-4-one (34.8 g) as pale yellow needles, mp 212–215° C.

Example 3

5-Iodo-2-(pyridin-2-yl)-6-trifluoromethyl-3H-pyrimidin-4-one 2-(Pyridin-2-yl)-6-trifluoromethyl-3H-pyrimidin-4-one (15.0 g) was dissolved in DMP (150 ml) and N-iodosuccinimide (33.6 g) was added at room temperature with stirring. The mixture was stirred under heating (130–135° C.) for 6 hr. and then cooled to room temperature. The reaction mixture was added ethyl acetate (150 ml), and then washed with aqueous sodium thiosulfate, water and brine, respectively. The ethyl acetate layer was dried over magnesium sulfate and the solvent was removed under reduced pressure to give crude 5-iodo-2-(pyridine-2-yl)-6-trifluoromethyl-3H-pyrimidin-4-one. It was recrystallized from toluene as pale brown needles (10.2 g), mp 186–187° C.

Example 4

4-Chloro-5-iodo-2-methylthio-6-trifluoromethylpyrimidine

5-Iodo-2-methylthio-6-trifluoromethyl-3H-pyrimidin-4-one (11.8 g) was dissolved in phosphoryl chloride (40 ml) and phosphorous pentachloride (7.9 g) was added at room temperature with stirring. The mixture was refluxed for 3 hr and the phosphoryl chloride was removed under reduced pressure. The residue was poured onto icy water and extracted with chloroform. The chloroform layer was washed with water and brine, respectively and dried over magnesium sulfate. The solvent was removed under reduced pressure to give 4-chloro-5-iodo-2-methylthio-6-trifluoromethylpyrimidine (12.2 g) as pale brown crystalline solid, mp 55–56° C.

Example 5

4-Chloro-5-iodo-2-isopropylsulfonyl-6-trifluoromethypyrimidine

4-Chloro-5-iodo-2-isopropylthio-6-trifluoromethypyrimidine (15.0 g) was dissolved in dichloromethane (150 ml) and m-chloroperbenzoic acid (75%, 27.1 g) was added portionwise under ice cooling with stirring. After stirring over night at room temperature, precipitated solid (m-chlorobenzoic acid) was removed by filtration. The reaction mixture was added aqueous sodium thiosulfate dropwise under ice cooling, then precipitated solid (m-chlorobenzoic acid) was removed by filtration again. The water layer was separated, and the dichloromethane layer was washed with aqueous sodium bicarbonate and brine, respectively and dried over magnesium sulfate. The solvent was removed under reduced pressure to give 4-chloro-5-iodo-2-isopropylsulfonyl-6-trifluoromethypyrimidine (14.3 g) as pale yellow crystalline solid, mp 67–69° C.

Example 6

5-Iodo-4-methoxy-2-methyl-6-trifluoromethylpyrimidine

4-Chloro-5-iodo-2-methyl-6-trifluoromethylpyrimidine (23.0 g) was dissolved in methanol (150 ml) and sodium methoxide (30% methanol solution, 12.8 g) was added under ice cooling with stirring. After stirring over night at room temperature, the solvent was removed under reduced pressure. The residue was mixed with water and extracted with benzene, and then benzene layer was washed with water and brine, respectively and dried over magnesium sulfate. The solvent was removed under reduced pressure, and the residue was purified by silica gel column chromatography (hexane-ethyl acetate). The crude fraction was concentrated, and then washed with cold hexane to give 5-iodo-4-methoxy-2-methyl-6-trifluoromethylpyrimidine (13.0 g) as colorless crystalline solid, mp 44–45° C.

Example 7

5-Ethynyl-4-methoxy-2-methylt-6-trifluoromethylpyrimidine

5-Iodo-4-methoxy-2-methyl-6-trifluoromethylpyrimidine (5.0 g) was dissolved in DMF (50 ml) and N,N-diisopropylethylamine (6.5 g), copper(I) iodide (0.3 g), dichlorobis(triphenylphosphine)palladium(II) (1.12 g) and trimethylsilylacetylene (15.4 g) was added at room temperature with stirring. The mixture was heated (50° C.) in nitrogen atmosphere for 7 hr and cool to room tempeature. The reaction mixture was added methyl tert-butyl ether (MTBE) (200 ml). The insoluble matter was removed by filtration through Celite and the filtrate was washed with water and brine, respectively. The MTBE solution was dried over magnesium sulfate and the solvent was removed under reduced pressure. The residue was purified by silica gel column chromatography (hexane-ethyl acetate) to give crude 4-methoxy-2-methyl-6-trifluoromethyl-5-trimethylsilylethynylpyrimidine (5.3 g) as pale yellow oil. This crude 4-methoxy-2-methyl-6-trifluoromethyl-5-trimethylsilylethynylpyrimidine (5.2 g) was dissolved in THF (100 ml) and tetrabutylammonium fluoride (1M THF solution, 18 ml) was added under ice cooling with stirring. After stirring 30 min at this temperature, the reaction mixture was added water in one portion under ice cooling and extracted with ethyl acetate. The ethyl acetate layer was washed with water and brine, respectively and dried over magnesium sulfate. The solvent was removed under reduced pressure. The residue was purified by silica gel column chromatography (hexane ethyl acetate) to give 5-ethynyl-4-methoxy-2-methyl-6-trifluoromethylpyrimidine (1.92 g) as colorless crystalline solid, mp 77° C.

Example 8

5-(1-Chlorovinyl)-2-methyl-6-trifluoromethyl-3H-pyrimidin-4-one 5-ethynyl-4-methoxy-2-methyl-6-trifluoromethylpyrimidine (1.92 g) was added 6N-HCl (20 ml) with stirring and refluxed for 2 hr. After cooling to room temperature, the reaction mixture was extracted with ethyl acetate. The ethyl acetate layer was washed with brine and dried over magnesium sulfate. The solvent was removed under reduced pressure. The residue was purified by silica gel column chromatography (hexanethyl acetate). The crude fraction was concentrated, and then washed with hexane to give 5-(1-chlorovinyl)-2-methyl-6-trifluoromethyl-3H-pyrimidin-4-one (1.62 g) as colorless crystalline solid, mp 164–166° C.

Example 9

5-Fluoro-2,4-dimethoxy-6-trifluoromethypyrimidine

5-Bromo-2,4-dimethoxy-6-trifluoromethypyrimidine (0.50 g) was dissolved in dry THF (5 ml) at room temperature under nitrogen atmosphere. The mixture was cooled to −70° C., and then added n-butyllithium (1.6M in hexane, 1.2 ml) dropwise below −50° C., and then added N-fluorobisphenylsulfonimide (0.61 g) TBF (5 ml) solution at once and the temperature was raised up to room temperature and then added water. The reaction mixture was extacted with benzene. The benzene layer was washed with water and brine, respectively and dried over magnesium sulfate. The solvent was removed under reduced pressure to give 5-fluoro-2,4-dimethoxy-6-trifluoromethypyrimidine (0.30 g) as pale yellow oil, ESI-MS 227 [M+H]$^+$.

Example 10

4-Cyano-5-iodo-2-methylthio-6-trifluoromethylpyrimidine

4-Chloro-5-iodo-2-methylthio-6-trifluoromethylpyrimidine (5.00 g) was dissolved in propionitrile (125 ml) and 4-(dimethylamino)-pyridine (1.81 g) was added at room temperature with stirring. After several minutes, precipitates appeared, however, it was stirred over night at room temperature. The slurry was cooled to ice bath temperature, and then added sodium cyanide (1.04 g) water (10 ml) solution. The mixture was warmed to room temperature and stirred 3 hr. The reaction mixture was added water and extracted with ethyl acetate. The ethyl acetate layer was washed with water and brine, respectively and dried over magnesium sulfate. The solvent was removed under reduced pressure. The residue was purified by silica get column chromatography (hexane-ethyl acetate) to give 4-cyano-5-iodo-2-methylthio-6-trifluoromiethylpyrimidine (2.56 g) as yellow solid, mp 68–69° C.

Example 11

4-Imidazol-1-yl-5-iodo-2-isopropylthio-6-trifluoromehyl-pyrimidine

4-Chloro-5-iodo-2-isopropylthio-6-trifluoromethylpyrimidine (3.0 g) was dissolved in acetonitrile (30 ml) and imidazole (1.6 g) was added at room temperature with stirring. The mixture was refluxed fbr 3 hr and then the solvent was removed under reduced pressure. The residue was added water and precipitates was filtered off to give crude 4-imidazol-1-yl-5-iodo-2-isopropylthio-6-trifluoromethyl-pyrimidine. It was recryslized from methanol-water mixture as colorless needles (2.61 g), mp 118–120° C.

Example 12

Ethyl 1-(5-iodo-2-isopropylthio-6-trifluororethylpyrimidin-4-yl)-3-trifluoromethyl-1H-pyrazol-4-carboxylate 4-Chloro-5-iodo-2-isopropylthio-6-trifluoromethylpyrimidine (0.30 g) was dissolved in dimethylsulfoxide (3.0 ml) and ethyl 3-trifluoromethyl-1H-pyrazole-4-carboxylate (0.16 g) and 1,8-diazabicyclo-[5,4,0]-under-7-ene (0.12 g) was added at room temperature with stirring. The mixture was heated to 80° C. and stirred for 2 hr. After cooling to room temperature, the mixture was added water and extracted with benzene. The benzene layer was washed with water and brine, respectively and dried over magnesium sulfate. The solvent was removed under reduced pressure. The residue was purified by silica gel column chromatography (hexane-ethyl acetate) to give ethyl 1-(5-iodo-2-isopropylthio-6-trifluoromethylpyrimidin-4-yl)-3-trifluoromethyl-1H-pyrazole-4-carboxylate (0.30 g) as colorless crystalline solid, mp 107–108° C.

Example 13

4-Imidazol-1-yl-5-iodo-2-prop-2-ynyloxy-6-trifluoromethyl-pyrimidine

4-Chloro-5-iodo-2-isopropylsulfonyl-6-trifluoromethypyrimidine (0.79 g) was dissolved in tetrahydrofuran (5.0 ml) and added propargyl alcohol (0.11 g). The mixture was cooled to ice bath temperature and added sodium hydride (oily 80%, 57 mg). The mixture was stirred at that temperature for 10 minutes, and then added imidazole (0.39 g) at the same temperature. The mixture was stirred at that temperature for 30 minutes, and then it warmed to room temperature. After stirring over night, the mixture was added water and extracted with ethyl acetate. The ethyl acetate layer was washed with water and brine, respectively and dried over magnesium sulfate. The solvent was removed under reduced pressure. The residue was purified by silica gel column chromatography (chloroform-THF). The fraction was triturated by hexane to give 4-imidazol-1-yl-5-iodo-2-prop-2-ynyloxy-6-trifluoromethyl-pyrimidine (0.20 g) as colorless crystalline solid, mp 128–129° C.

Example 14

1-(4-Imidazol-1-yl-5-iodo-6-trifluoromethylpyrimidin-2-yl)-pyrrolidin-2-one

4-Chloro-5-iodo-2-isopropylsulfonyl-6-trifluoromethypyrimidine (0.50 g) was dissolved in tetrahydrofuran (5.0 ml) and added 2-pyrrolidinone (0.10 g). The mixture was cooled to ice bath temperature and added sodium hydride (oily 80%, 36 mg). The mixture was stirred at that temperature for 10 minutes, and then added imidazole (0.25 g) at the same temperature. The mixture was stirred at that temperature for 30 minutes, and then it warmed to room temperature After stirg over night, the mixture was added water and extracted with ethyl acetate. The ethyl acetate layer was washed with water and brine, respectively and dried over magnesium sulfate. The solvent was removed under reduced pressure. The residue was purified by silica gel column chromatography (chloroform-THF) to give 1-(4-imidazol-1-yl-5-iodo-6-trifluoromethylpyrimidin-2-yl)-pyrrolidin-2-one (0.20 g) as colorless crystalline solid, mp 195–197° C.

Example 15

5-Iodo-2-methylthio-4-(2H-tetrazol-5-yl)-6-trifluoromethyl-pyrimidine

4-Cyano-5-iodo-2-methylthio-6-trifluoromethylpyrimidine (0.50 g) was dissolved in isopropanol (5 ml) and added water (10 ml), sodium azide (0.19 g) and zinc bromide (0.16 g) with stirring in room temperature. The mixture was refluxed for 3 hr and then cooled to room temperature and then added 3N-HCl to acidify. The mixture was extracted with ethyl acetate. The ethyl acetate layer was washed with water and brine, respectively and dried over magnesium sulfate. The solvent was removed under reduced pressure to give 5-iodo-2-methylthio-4-(2H-tetrazol-5-yl)-6-trifluoromethyl-pyrimidine (0.5 g) as colorless crystalline solid, mp 196–200° C.

Example 16

5-Iodo-2-methylthio-4-(2-methyl-2H-tetrazol-5-yl)-6-trifluoromethyl-pyrimidine

5-Iodo-2-methylthio-4-(2H-tetrazol-5-yl)trifluoromethyl-pyrimidine (0.25 g) was added benzene (4 ml) and methanol (1 ml). The mixture was added trimethylsilyldiazomethane (2M in hexane, 1 ml) at room temperature dropwise and stirred over night. The solvent was removed under reduced pressure to give crude 5-iodo-2-methylthio-4-(2-methyl-2H-tetrazol-5-yl)-4-trifluoromethyl-pyrimidine. It was recrystallized from hexane-benzene as colorless crystalline solid, mp 113–118° C.

Example 17

5-(1-Chlorovinyl)-4-imidazol-1-yl-2-methyl-6-trifluoromethyl-pyrimidine

4-Chloro-5-(1-chlorovinyl)-2-methyl-6-trifluoromethyl-pyrimidine (1.83 g) was dissolved in acetonitrile (20 ml) under stirring in room temperature. The mixture was added imidazole (1.45 g) and refluxed 3 hr and then cooled to room temperature and added water. The mixture was extracted with chloroform. The chloroform layer was washed with water and brine, respectively and dried over magnesium sulfate. The solvent was removed under reduced pressure. The residue was purified by silica gel column chromatography (chloroform-THF) to give 5-(1-chlorovinyl)-4-imidazol-1-yl-2-methyl-6-trifluoromethyl-pyrimidine (1.34 g) as pale brown oil. $^1$H-NMR (δ, ppm); 2.82 (s, 3H), 5.78 (d, 1H), 6.03 (d, 1H), 7.21 (br, 1H), 7.87 (br, 1H), 8.55 (br, 1H).

Example 18

5-Ethynyl-4-imidazol-1-yl-2-methyl-6-trifluoromethylpyrimidine 5-(1-Chlorovinyl)-4-imidazol-1-yl-2-methyl-6-trifluoromethyl-pyrimidine (0.20 g) was dissolved in dimethylsulfoxide (2 ml) and 1,8-diazabicyclo-[5,4,0]-undec-7-ene (0.11 g) was added at room temperature with stirring. The mixture was stirred for 2 hr in room temperature and then added water. The mixture was extracted with ethyl acetate. The ethyl acetate layer was washed water and brine, respectively and dried over magnesium sulfate. The solvent was removed under reduced pressure. The residue was purified by silica gel column chromatography (chloroform-THF) to give 5-Ethynyl-4-imidazol-1-yl-2-methyl-6-trifluoromethylpyrimidine (0.11 g) as colorless crystalline solid, mp 121–122° C.

Example 19

5-Fluoro-2,4-diimidazol-1-yl-6-trifluoromethylpyrimidine 2,4-Dichloro-5-fluoro-6-trifluoromethylpyrimidine (2.74 g) was dissolved in acetonitrile (30 ml) and imidazole (3.97 g) was added at room temperature with stirring. The mixture was stirred over night and then the solvent was removed under reduced pressure. The residue was added water and extracted with ethyl acetate. The ethyl acetate layer was washed with water and brine, respectively and dried over magnesium sulfate. The solvent was removed under reduced pressure. The residue was triturated with carbon tetrachloride to give crude, 5-fluoro-2,4-diimidazol-1-yl-6-trifluoromethylpyrimidine. It was recrystallized from isopropanol as colorless crystalline solid, mp 142–150° C. (decomposed).

Test Example 1

Test on Apple Scab Control (Preventive Application)

The emulsifiable concentrate prepared for the compound according to the present invention was diluted so as to prepared the solution at a concentration of 100 ppm, and the diluted solution was the sprayed to apple young trees (variety, Kokko, at 3–4 leaf stage) grown in an unglazed pot. The spayed solution was naturally dried, then conidia of apple scab fungus (*Venturia inaequalis*) were inoculated onto the test apples. The inoculated apple trees were placed in a room being maintained at 20° C. and high humidity with repeated lighting of 12 hours intervals, and the apple trees are allowed to stand in the room for two weeks. After that period, assessment was made to determine the control efficacy by checking the infestation degree by the fungus on the leaves in comparison with the control apple trees. As a result, the compounds having the following compound numbers showed to have excellent control performance value higher than 75% on the disease. Note that the compound numbers in the following correspond to the same compound numbers in the Table 1.

Compound Nos.; 47, 48, 54, 68, 78, 86, 90, 128, 145, 238, 256, 274, 292, 328, 346, 401, 474, 531, 568, 586

Test Example 2

Test on Kidney Bean Gray Mold Control

Flowers of Kidney bean (variety; Nagauzura) grown in a flat vessel for culturing seedlings were cut, and the cut flowers were dipped into a solution prepared by diluting the emulsifiable concentrate prepared fbr the compound of the present invention at a concentration of 100 ppm based on the active ingredient. After the dipping, the flowers were dried at a room temperature. Then, spore solution of snap bean gray mold fuingus (*Botrytis cinerea*) was sprayed to the flowers. The flowers sprayed with spores of the gray mold fungus were placed on the leaves which were detached from healthy Kidney bean plants, and those leaves were placed in a room being maintained at 20° C. and high humidity with repeated lighting of 12 hours intervals, and the Kidney bean leaves were incubated in the room for 7 days. Then, the infestation degree by the fungus on the leaves was checked in comparison to the control healthy leaves to determine the control efficacy. As a result, the compounds of the following compound numbers showed to have excellent control performance. Note that the compound numbers in the following correspond to the same compound numbers in the Table 1.
Compound Nos.; 47, 48, 54, 68, 90, 184, 238, 256, 274, 292, 531, 568

Test Example 3

Test on *Pythium aphanidermatum* "In Vitro" Control of Growth

The compound was prepared according to the present invention was diluted to achieve a final concentration of 100 ppm, and the diluted solution was used to saturate ½ inch-diameter, cellulose discs (Schleicher & Schuell catalog #740-E). The treated cellulose discs were then air dried for 90 minutes in a class 11 biosafety cabinet to eliminate external free moisture. Replicated treated discs and untreated discs were placed onto Difco Corn meal agar in 80 mm plastic petri plates. The discs (2 treated and one untreated in each of two petri plates) were each inoculated with a 4 mm square block of agar containing an actively growing culture of *Pythium aphanidermatum*. The inoculated plates were incubated at 23° C. with diurnal lighting with 12 hour intervals. Radial growth of *Pythium aphanidermatum* on the treated and untreated discs was measured at 24 and 48 hours after inoculation. Percent of growth inhibition was determined by comparing radial growth on the untated check discs to the growth on the treated discs. As a result, the compounds listed below had an excellent suppression performance value compared to the untreated check. Note that the compound numbers listed below correspond to the same compound numbers in Table 1.
Compound Nos.; 1, 47, 256, 346, 401, 474, 531, 586

Test Example 4

Test on *Sclerotinia sclerotiorum* "In Vitro" Control of Growth

The compound prepared according to the present invention was diluted to achieve a final concentration of 100 ppm, and the diluted solution was used to satrate ½ inch-diameter, cellulose discs (Schleicher & Schuell catalog #740-E). The treated cellulose discs were then air dried for 90 minutes in a class II biosafety cabinet to eliminate external free moisture. Replicated treated discs and untreated discs were placed onto acidified Difco Potato Dextrose agar in 80 mm plastic petri plates. The discs (2 treated and one untrtated in each of two petri plates) were each inoculated with a 4 mm square block of agar containing an actively growing culture of *Sclerotinia sclerotiorum*. The inoculated plates were incubated at 23° C. with diurnal lighting with 12 hour intervals. Radial growth of *Sclerotinia sclerotiorum* on the treated and untreated discs was measured at 48 and 96 hours after inoculation. Percent of growth inhibition was determined by comparing radial growth on the untreated check discs to the growth on the treated discs. As a result, the compounds listed below had an excellent suppression performance value compared to the untreated check. Note that the compound numbers listed below correspond to the same compound numbers in Table 1.
Compound Nos. 1, 47, 48, 128, 145, 256, 401, 474, 531, 568, 586

TABLE 1

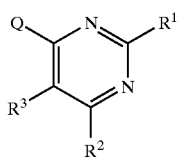

(1)

| No. | R1 | R2 | R3 | Q | mp (° C.) |
|---|---|---|---|---|---|
| 1 | SCH3 | CF3 | I | 1,2,4-triazol-1-yl | 93–94 |
| 2 | SCH3 | CF2CF3 | I | 1,2,4-triazol-1-yl | |
| 3 | SCH3 | CF3 | I | 2H-tetrazol-5-yl | 196–200 dec |
| 4 | SCH3 | CF2CF3 | I | 2H-tetrazol-5-yl | |
| 5 | SCH3 | CF3 | I | 2-methyl-2H-tetrazol-5-yl | 113–118 |
| 6 | SCH3 | CF2CF3 | I | 2-methyl-2H-tetrazol-5-yl | |
| 7 | SCH3 | CF3 | I | 3-(p-acetoxybenzylthio)-1,2,4-triazol-1-yl | |
| 8 | SCH3 | CF3 | I | 3-amino-1,2,4-triazol-1-yl | |
| 9 | SCH3 | CF3 | I | 3-bromo-1,2,4-triazol-1-yl | |
| 10 | SCH3 | CF3 | I | 3-chloro-1,2,4-triazol-1-yl | |
| 11 | SCH3 | CF3 | I | 3-cyano-1,2,4-triazol-1-yl | |
| 12 | SCH3 | CF3 | I | 3-fluoro-1,2,4-triazol-1-yl | |
| 13 | SCH3 | CF3 | I | 3-hydroxy-1,2,4-triazol-1-yl | |
| 14 | SCH3 | CF3 | I | 3-mercapto-1,2,4-triazol-1-yl | |
| 15 | SCH3 | CF3 | I | 3-methoxy-1,2,4-triazol-1-yl | |
| 16 | SCH3 | CF3 | I | 3-methylamino-1,2,4-triazol-1-yl | |
| 17 | SCH3 | CF3 | I | 3-methylthio-1,2,4-triazol-1-yl | |
| 18 | SCH3 | CF3 | I | 3-trifluoromethyl-1,2,4-triazol-1-yl | |
| 19 | SCH3 | CF3 | I | 5-(p-acetoxybenzylthio)imidazol-1-yl | |
| 20 | SCH3 | CF3 | I | 5-(p-acetoxybenzylthio)-1,2,4-triazol-1-yl | 141–143 |

TABLE 1-continued (1)

$$\begin{array}{c}\text{Q}\diagdown\text{N}\diagup\text{R}^1\\ \text{R}^3\diagdown\diagdown\text{N}\\ \text{R}^2\end{array}$$

| No. | R1 | R2 | R3 | Q | mp (° C.) |
|---|---|---|---|---|---|
| 21 | SCH3 | CF3 | I | 4-aminoimidazol-1-yl | |
| 22 | SCH3 | CF3 | I | 5-amino-1,2,4-triazol-1-yl | |
| 23 | SCH3 | CF3 | I | 4-bromoimidazol-1-yl | |
| 24 | SCH3 | CF3 | I | 5-bromo-1,2,4-triazol-1-yl | |
| 25 | SCH3 | CF3 | I | 4-chloroimidazol-1-yl | |
| 26 | SCH3 | CF3 | I | 5-chloro-1,2,4-triazol-1-yl | |
| 27 | SCH3 | CF3 | I | 4-cyanoimidazol-1-yl | |
| 28 | SCH3 | CF3 | I | 5-cyano-1,2,4-triazol-1-yl | |
| 29 | SCH3 | CF3 | I | 4-fluoroimidazol-1-yl | |
| 30 | SCH3 | CF3 | I | 5-fluoro-1,2,4-triazol-1-yl | |
| 31 | SCH3 | CF3 | I | 4-hydroxyimidazol-1-yl | |
| 32 | SCH3 | CF3 | I | 5-hydroxy-1,2,4-triazol-1-yl | |
| 33 | SCH3 | CF3 | I | 4-mercaptoimidazol-1-yl | |
| 34 | SCH3 | CF3 | I | 5-mercapto-1,2,4-triazol-1-yl | |
| 35 | SCH3 | CF3 | I | 4-methoxyimidazol-1-yl | |
| 36 | SCH3 | CF3 | I | 5-methoxy-1,2,4-triazol-1-yl | |
| 37 | SCH3 | CF3 | I | 4-methylaminoimidazol-1-yl | |
| 38 | SCH3 | CF3 | I | 5-methylamino-1,2,4-triazol-1-yl | |
| 39 | SCH3 | CF3 | I | 4-methylimidazol-1-yl | 147–148 |
| 40 | SCH3 | CF2CF3 | I | 4-methylimidazol-1-yl | |
| 41 | SCH3 | CF3 | I | 4-methylthioimidazol-1-yl | |
| 42 | SCH3 | CF3 | I | 5-methylthio-1,2,4-triazol-1-yl | |
| 43 | SCH3 | CF3 | I | 4-trifluoromethylimidazol-1-yl | |
| 44 | SCH3 | CF3 | I | 5-trifluoromethyl-1,2,4-triazol-1-yl | |
| 45 | SCH3 | CF3 | I | benzimidazol-1-yl | 128 |
| 46 | SCH3 | CF2CF3 | I | benzimidazol-1-yl | |
| 47 | SCH3 | CF3 | I | imidazol-1-yl | 137–139 |
| 48 | SCH3 | CF2CF3 | I | imidazol-1-yl | 112–114 |
| 49 | SCH3 | CF3 | I | pyrazol-1-yl | 115–116 |
| 50 | SCH3 | CF3 | F | 2H-tetrazol-5-yl | |
| 51 | SCH3 | CF3 | F | 2-methyl-2H-tetrazol-5-yl | |
| 52 | SCH3 | CF3 | Cl | 2H-tetrazol-5-yl | 177–178 |
| 53 | SCH3 | CF3 | Cl | 2-methyl-2H-tetrazol-5-yl | 128–130 |
| 54 | SCH3 | CF3 | Br | 1,2,4-triazol-1-yl | 85–87 |
| 55 | SCH3 | CF3 | Br | 2H-tetrazol-5-yl | 192–193 |
| 56 | SCH3 | CF3 | Br | 2-methyl-2H-tetrazol-5-yl | 102–105 |
| 57 | SCH3 | CF3 | Br | imidazol-1-yl | 89–90 |
| 58 | SCH2CH3 | CF3 | I | 1,2,4-triazol-1-yl | |
| 59 | SCH2CH3 | CF2CF3 | I | 1,2,4-triazol-1-yl | |
| 60 | SCH2CH3 | CF3 | I | 2H-tetrazol-5-yl | |
| 61 | SCH2CH3 | CF2CF3 | I | 2H-tetrazol-5-yl | |
| 62 | SCH2CH3 | CF3 | I | 2-methyl-2H-tetrazol-5-yl | |
| 63 | SCH2CH3 | CF2CF3 | I | 2-methyl-2H-tetrazol-5-yl | |
| 64 | SCH2CH3 | CF3 | I | 4-methylimidazol-1-yl | |
| 65 | SCH2CH3 | CF2CF3 | I | 4-methylimidazol-1-yl | |
| 66 | SCH2CH3 | CF3 | I | benzimidazol-1-yl | |
| 67 | SCH2CH3 | CF2CF3 | I | benzimidazol-1-yl | |
| 68 | SCH2CH3 | CF3 | I | imidazol-1-yl | 106–109 |
| 69 | SCH2CH3 | CF2CF3 | I | imidazol-1-yl | |
| 70 | SCH2CH3 | CF3 | F | 2H-tetrazol-5-yl | |
| 71 | SCH2CH3 | CF3 | F | 2-methyl-2H-tetrazol-5-yl | |
| 72 | SCH2CH3 | CF3 | Cl | 2H-tetrazol-5-yl | |
| 73 | SCH2CH3 | CF3 | Cl | 2-methyl-2H-tetrazol-5-yl | |
| 74 | SCH2CH3 | CF3 | Br | 2H-tetrazol-5-yl | |
| 75 | SCH2CH3 | CF3 | Br | 2-methyl-2H-tetrazol-5-yl | |
| 76 | SCH(CH3)2 | CF3 | I | 1,2,3-triazol-1-yl | 157–159 |
| 77 | SCH(CH3)2 | CF3 | I | 1,2,3-triazol-2-yl | 167–169 |
| 78 | SCH(CH3)2 | CF3 | I | 1,2,4-triazol-1-yl | 70–71 |
| 79 | SCH(CH3)2 | CF2CF3 | I | 1,2,4-triazol-1-yl | |
| 80 | SCH(CH3)2 | CF3 | I | 2H-tetrazol-5-yl | |
| 81 | SCH(CH3)2 | CF2CF3 | I | 2H-tetrazol-5-yl | |
| 82 | SCH(CH3)2 | CF3 | I | 2-methyl-2H-tetrazol-5-yl | |
| 83 | SCH(CH3)2 | CF2CF3 | I | 2-methyl-2H-tetrazol-5-yl | |
| 84 | SCH(CH3)2 | CF3 | I | 2-methylimidazol-1-yl | 133–135 |
| 85 | SCH(CH3)2 | CF3 | I | 4-ethoxycarbonyl-3-trifluoromethylpyrazol-1-yl | 107–108 |
| 86 | SCH(CH3)2 | CF3 | I | 4-methylimidazol-1-yl | 138–140 |

TABLE 1-continued (1)

$$\underset{R^3}{\overset{Q}{\underset{R^2}{\bigvee}}}\overset{N}{\underset{N}{\bigvee}}R^1$$

| No. | R1 | R2 | R3 | Q | mp (° C.) |
|---|---|---|---|---|---|
| 87 | SCH(CH3)2 | CF2CF3 | I | 4-methylimidazol-1-yl | |
| 88 | SCH(CH3)2 | CF3 | I | benzimidazol-1-yl | |
| 89 | SCH(CH3)2 | CF2CF3 | I | benzimidazol-1-yl | |
| 90 | SCH(CH3)2 | CF3 | I | imidazol-1-yl | 118–120 |
| 91 | SCH(CH3)2 | CF2CF3 | I | imidazol-1-yl | |
| 92 | SCH(CH3)2 | CF3 | F | 2H-tetrazol-5-yl | |
| 93 | SCH(CH3)2 | CF3 | F | 2-methyl-2H-tetrazol-5-yl | |
| 94 | SCH(CH3)2 | CF3 | Cl | 2H-tetrazol-5-yl | |
| 95 | SCH(CH3)2 | CF3 | Cl | 2-methyl-2H-tetrazol-5-yl | |
| 96 | SCH(CH3)2 | CF3 | Br | 2H-tetrazol-5-yl | |
| 97 | SCH(CH3)2 | CF3 | Br | 2-methyl-2H-tetrazol-5-yl | |
| 98 | S(O)2CH3 | CF3 | I | 1,2,4-triazol-1-yl | |
| 99 | S(O)2CH3 | CF2CF3 | I | 1,2,4-triazol-1-yl | |
| 100 | S(O)2CH3 | CF3 | I | 2H-tetrazol-5-yl | |
| 101 | S(O)2CH3 | CF2CF3 | I | 2H-tetrazol-5-yl | |
| 102 | S(O)2CH3 | CF3 | I | 2-methyl-2H-tetrazol-5-yl | |
| 103 | S(O)2CH3 | CF2CF3 | I | 2-methyl-2H-tetrazol-5-yl | |
| 104 | S(O)2CH3 | CF3 | I | 4-methylimidazol-1-yl | |
| 105 | S(O)2CH3 | CF2CF3 | I | 4-methylimidazol-1-yl | |
| 106 | S(O)2CH3 | CF3 | I | benzimidazol-1-yl | |
| 107 | S(O)2CH3 | CF2CF3 | I | benzimidazol-1-yl | |
| 108 | S(O)2CH3 | CF3 | I | imidazol-1-yl | |
| 109 | S(O)2CH3 | CF2CF3 | I | imidazol-1-yl | |
| 110 | S(O)2CH3 | CF3 | F | 2H-tetrazol-5-yl | |
| 111 | S(O)2CH3 | CF3 | F | 2-methyl-2H-tetrazol-5-yl | |
| 112 | S(O)2CH3 | CF3 | Cl | 2H-tetrazol-5-yl | |
| 113 | S(O)2CH3 | CF3 | Cl | 2-methyl-2H-tetrazol-5-yl | |
| 114 | S(O)2CH3 | CF3 | Br | 1,2,4-triazol-1-yl | 158–159 |
| 115 | S(O)2CH3 | CF3 | Br | 2H-tetrazol-5-yl | |
| 116 | S(O)2CH3 | CF3 | Br | 2-methyl-2H-tetrazol-5-yl | |
| 117 | pyridin-4-yl | CF3 | I | 1,2,4-triazol-1-yl | |
| 118 | pyridin-4-yl | CF2CF3 | I | 1,2,4-triazol-1-yl | |
| 119 | pyridin-4-yl | CF3 | I | 2H-tetrazol-5-yl | |
| 120 | pyridin-4-yl | CF2CF3 | I | 2H-tetrazol-5-yl | |
| 121 | pyridin-4-yl | CF3 | I | 2-methyl-2H-tetrazol-5-yl | |
| 122 | pyridin-4-yl | CF2CF3 | I | 2-methyl-2H-tetrazol-5-yl | |
| 123 | pyridin-4-yl | CF3 | I | 4-methylimidazol-1-yl | |
| 124 | pyridin-4-yl | CF2CF3 | I | 4-methylimidazol-1-yl | |
| 125 | pyridin-4-yl | CF3 | I | benzimidazol-1-yl | |
| 126 | pyridin-4-yl | CF2CF3 | I | benzimidazol-1-yl | |
| 127 | pyridin-4-yl | CF2CF3 | I | imidazol-1-yl | |
| 128 | pyridin-4-yl | CF3 | I | imidazol-1-yl | 230 dec |
| 129 | pyridin-4-yl | CF3 | F | 2H-tetrazol-5-yl | |
| 130 | pyridin-4-yl | CF3 | F | 2-methyl-2H-tetrazol-5-yl | |
| 131 | pyridin-4-yl | CF3 | Cl | 2H-tetrazol-5-yl | |
| 132 | pyridin-4-yl | CF3 | Cl | 2-methyl-2H-tetrazol-5-yl | |
| 133 | pyridin-4-yl | CF3 | Br | 2H-tetrazol-5-yl | |
| 134 | pyridin-4-yl | CF3 | Br | 2-methyl-2H-tetrazol-5-yl | |
| 135 | pyridin-2-yl | CF3 | I | 1,2,4-triazol-1-yl | 169–171 |
| 136 | pyridin-2-yl | CF2CF3 | I | 1,2,4-triazol-1-yl | |
| 137 | pyridin-2-yl | CF3 | I | 2H-tetrazol-5-yl | |
| 138 | pyridin-2-yl | CF2CF3 | I | 2H-tetrazol-5-yl | |
| 139 | pyridin-2-yl | CF3 | I | 2-methyl-2H-tetrazol-5-yl | |
| 140 | pyridin-2-yl | CF2CF3 | I | 2-methyl-2H-tetrazol-5-yl | |
| 141 | pyridin-2-yl | CF3 | I | 4-methylimidazol-1-yl | |
| 142 | pyridin-2-yl | CF2CF3 | I | 4-methylimidazol-1-yl | |
| 143 | pyridin-2-yl | CF3 | I | benzimidazol-1-yl | |
| 144 | pyridin-2-yl | CF2CF3 | I | benzimidazol-1-yl | |
| 145 | pyridin-2-yl | CF3 | I | imidazol-1-yl | 243–245 |
| 146 | pyridin-2-yl | CF2CF3 | I | imidazol-1-yl | |
| 147 | pyridin-2-yl | CF3 | I | pyrazol-1-yl | 145–146 |
| 148 | pyridin-2-yl | CF3 | F | 2H-tetrazol-5-yl | |
| 149 | pyridin-2-yl | CF3 | F | 2-methyl-2H-tetrazol-5-yl | |
| 150 | pyridin-2-yl | CF3 | Cl | 2H-tetrazol-5-yl | |
| 151 | pyridin-2-yl | CF3 | Cl | 2-methyl-2H-tetrazol-5-yl | |
| 152 | pyridin-2-yl | CF3 | Cl | imidazol-1-yl | 129–130 |

TABLE 1-continued (1)

| No. | R1 | R2 | R3 | Q | mp (° C.) |
|---|---|---|---|---|---|
| 153 | pyridin-2-yl | CF3 | Br | 2H-tetrazol-5-yl | |
| 154 | pyridin-2-yl | CF3 | Br | 2-methyl-2H-tetrazol-5-yl | |
| 155 | pyridin-2-yl | CF3 | Br | imidazol-1-yl | 140 |
| 156 | pyrazol-1-yl | CF3 | I | 1,2,4-triazol-1-yl | |
| 157 | pyrazol-1-yl | CF2CF3 | I | 1,2,4-triazol-1-yl | |
| 158 | pyrazol-1-yl | CF3 | I | 2H-tetrazol-5-yl | |
| 159 | pyrazol-1-yl | CF2CF3 | I | 2H-tetrazol-5-yl | |
| 160 | pyrazol-1-yl | CF3 | I | 2-methyl-2H-tetrazol-5-yl | |
| 161 | pyrazol-1-yl | CF2CF3 | I | 2-methyl-2H-tetrazol-5-yl | |
| 162 | pyrazol-1-yl | CF3 | I | 4-methylimidazol-1-yl | |
| 163 | pyrazol-1-yl | CF2CF3 | I | 4-methylimidazol-1-yl | |
| 164 | pyrazol-1-yl | CF3 | I | benzimidazol-1-yl | |
| 165 | pyrazol-1-yl | CF2CF3 | I | benzimidazol-1-yl | |
| 166 | pyrazol-1-yl | CF3 | I | imidazol-1-yl | 175–180 dec |
| 167 | pyrazol-1-yl | CF2CF3 | I | imidazol-1-yl | |
| 168 | pyrazol-1-yl | CF3 | F | 2H-tetrazol-5-yl | |
| 169 | pyrazol-1-yl | CF3 | F | 2-methyl-2H-tetrazol-5-yl | |
| 170 | pyrazol-1-yl | CF3 | Cl | 2H-tetrazol-5-yl | |
| 171 | pyrazol-1-yl | CF3 | Cl | 2-methyl-2H-tetrazol-5-yl | |
| 172 | pyrazol-1-yl | CF3 | Br | 2H-tetrazol-5-yl | |
| 173 | pyrazol-1-yl | CF3 | Br | 2-methyl-2H-tetrazol-5-yl | |
| 174 | phenyl | CF3 | I | 1,2,4-triazol-1-yl | |
| 175 | phenyl | CF2CF3 | I | 1,2,4-triazol-1-yl | |
| 176 | phenyl | CF3 | I | 2H-tetrazol-5-yl | |
| 177 | phenyl | CF2CF3 | I | 2H-tetrazol-5-yl | |
| 178 | phenyl | CF3 | I | 2-methyl-2H-tetrazol-5-yl | |
| 179 | phenyl | CF2CF3 | I | 2-methyl-2H-tetrazol-5-yl | |
| 180 | phenyl | CF3 | I | 4-methylimidazol-1-yl | |
| 181 | phenyl | CF2CF3 | I | 4-methylimidazol-1-yl | |
| 182 | phenyl | CF3 | I | benzimidazol-1-yl | |
| 183 | phenyl | CF2CF3 | I | benzimidazol-1-yl | |
| 184 | phenyl | CF3 | I | imidazol-1-yl | 179–180 |
| 185 | phenyl | CF2CF3 | I | imidazol-1-yl | |
| 186 | phenyl | CF3 | F | 2H-tetrazol-5-yl | |
| 187 | phenyl | CF3 | F | 2-methyl-2H-tetrazol-5-yl | |
| 188 | phenyl | CF3 | Cl | 2H-tetrazol-5-yl | |
| 189 | phenyl | CF3 | Cl | 2-methyl-2H-tetrazol-5-yl | |
| 190 | phenyl | CF3 | Br | 2H-tetrazol-5-yl | |
| 191 | phenyl | CF3 | Br | 2-methyl-2H-tetrazol-5-yl | |
| 192 | OCH3 | CF3 | I | 1,2,4-triazol-1-yl | |
| 193 | OCH3 | CF2CF3 | I | 1,2,4-triazol-1-yl | |
| 194 | OCH3 | CF3 | I | 2H-tetrazol-5-yl | |
| 195 | OCH3 | CF2CF3 | I | 2H-tetrazol-5-yl | |
| 196 | OCH3 | CF3 | I | 2-methyl-2H-tetrazol-5-yl | |
| 197 | OCH3 | CF2CF3 | I | 2-methyl-2H-tetrazol-5-yl | |
| 198 | OCH3 | CF3 | I | 3-(p-acetoxybenzylthio)-1,2,4-triazol-1-yl | |
| 199 | OCH3 | CF3 | I | 3-amino-1,2,4-triazol-1-yl | |
| 200 | OCH3 | CF3 | I | 3-bromo-1,2,4-triazol-1-yl | |
| 201 | OCH3 | CF3 | I | 3-chloro-1,2,4-triazol-1-yl | |
| 202 | OCH3 | CF3 | I | 3-cyano-1,2,4-triazol-1-yl | |
| 203 | OCH3 | CF3 | I | 3-fluoro-1,2,4-triazol-1-yl | |
| 204 | OCH3 | CF3 | I | 3-hydroxy-1,2,4-triazol-1-yl | |
| 205 | OCH3 | CF3 | I | 3-mercapto-1,2,4-triazol-1-yl | |
| 206 | OCH3 | CF3 | I | 3-methoxy-1,2,4-triazol-1-yl | |
| 207 | OCH3 | CF3 | I | 3-methylamino-1,2,4-triazol-1-yl | |
| 208 | OCH3 | CF3 | I | 3-methylthio-1,2,4-triazol-1-yl | |
| 209 | OCH3 | CF3 | I | 3-trifluoromethyl-1,2,4-triazol-1-yl | |
| 210 | OCH3 | CF3 | I | 5-(p-acetoxybenzylthio)imidazol-1-yl | |
| 211 | OCH3 | CF3 | I | 5-(p-acetoxybenzylthio)-1,2,4-triazol-1-yl | |
| 212 | OCH3 | CF3 | I | 4-aminoimidazol-1-yl | |
| 213 | OCH3 | CF3 | I | 5-amino-1,2,4-triazol-1-yl | |
| 214 | OCH3 | CF3 | I | 4-bromoimidazol-1-yl | |
| 215 | OCH3 | CF3 | I | 5-bromo-1,2,4-triazol-1-yl | |
| 216 | OCH3 | CF3 | I | 4-chloroimidazol-1-yl | |
| 217 | OCH3 | CF3 | I | 5-chloro-1,2,4-triazol-1-yl | |
| 218 | OCH3 | CF3 | I | 4-cyanoimidazol-1-yl | |

TABLE 1-continued (1)

| No. | R1 | R2 | R3 | Q | mp (° C.) |
|---|---|---|---|---|---|
| 219 | OCH3 | CF3 | I | 5-cyano-1,2,4-triazol-1-yl | |
| 220 | OCH3 | CF3 | I | 4-fluoroimidazol-1-yl | |
| 221 | OCH3 | CF3 | I | 5-fluoro-1,2,4-triazol-1-yl | |
| 222 | OCH3 | CF3 | I | 4-hydroxyimidazol-1-yl | |
| 223 | OCH3 | CF3 | I | 5-hydroxy-1,2,4-triazol-1-yl | |
| 224 | OCH3 | CF3 | I | 4-mercaptoimidazol-1-yl | |
| 225 | OCH3 | CF3 | I | 5-mercapto-1,2,4-triazol-1-yl | |
| 226 | OCH3 | CF3 | I | 4-methoxyimidazol-1-yl | |
| 227 | OCH3 | CF3 | I | 5-methoxy-1,2,4-triazol-1-yl | |
| 228 | OCH3 | CF3 | I | 4-methylaminoimidazol-1-yl | |
| 229 | OCH3 | CF3 | I | 5-methylamino-1,2,4-triazol-1-yl | |
| 230 | OCH3 | CF3 | I | 4-methylimidazol-1-yl | |
| 231 | OCH3 | CF2CF3 | I | 4-methylimidazol-1-yl | |
| 232 | OCH3 | CF3 | I | 4-methylthioimidazol-1-yl | |
| 233 | OCH3 | CF3 | I | 5-methylthio-1,2,4-triazol-1-yl | |
| 234 | OCH3 | CF3 | I | 4-trifluoromethylimidazol-1-yl | |
| 235 | OCH3 | CF3 | I | 5-trifluoromethyl-1,2,4-triazol-1-yl | |
| 236 | OCH3 | CF3 | I | benzimidazol-1-yl | |
| 237 | OCH3 | CF2CF3 | I | benzimidazol-1-yl | |
| 238 | OCH3 | CF3 | I | imidazol-1-yl | 111–113 |
| 239 | OCH3 | CF2CF3 | I | imidazol-1-yl | |
| 240 | OCH3 | CF3 | F | 2H-tetrazol-5-yl | |
| 241 | OCH3 | CF3 | F | 2-methyl-2H-tetrazol-5-yl | |
| 242 | OCH3 | CF3 | Cl | 2H-tetrazol-5-yl | |
| 243 | OCH3 | CF3 | Cl | 2-methyl-2H-tetrazol-5-yl | |
| 244 | OCH3 | CF3 | Br | 2H-tetrazol-5-yl | |
| 245 | OCH3 | CF3 | Br | 2-methyl-2H-tetrazol-5-yl | |
| 246 | OCH2C°CH | CF3 | I | 1,2,4-triazol-1-yl | |
| 247 | OCH2C°CH | CF2CF3 | I | 1,2,4-triazol-1-yl | |
| 248 | OCH2C°CH | CF3 | I | 2H-tetrazol-5-yl | |
| 249 | OCH2C°CH | CF2CF3 | I | 2H-tetrazol-5-yl | |
| 250 | OCH2C°CH | CF3 | I | 2-methyl-2H-tetrazol-5-yl | |
| 251 | OCH2C°CH | CF2CF3 | I | 2-methyl-2H-tetrazol-5-yl | |
| 252 | OCH2C°CH | CF3 | I | 4-methylimidazol-1-yl | |
| 253 | OCH2C°CH | CF2CF3 | I | 4-methylimidazol-1-yl | |
| 254 | OCH2C°CH | CF3 | I | benzimidazol-1-yl | |
| 255 | OCH2C°CH | CF2CF3 | I | benzimidazol-1-yl | |
| 256 | OCH2C°CH | CF3 | I | imidazol-1-yl | 128–129 |
| 257 | OCH2C°CH | CF2CF3 | I | imidazol-1-yl | |
| 258 | OCH2C°CH | CF3 | F | 2H-tetrazol-5-yl | |
| 259 | OCH2C°CH | CF3 | F | 2-methyl-2H-tetrazol-5-yl | |
| 260 | OCH2C°CH | CF3 | Cl | 2H-tetrazol-5-yl | |
| 261 | OCH2C°CH | CF3 | Cl | 2-methyl-2H-tetrazol-5-yl | |
| 262 | OCH2C°CH | CF3 | Br | 2H-tetrazol-5-yl | |
| 263 | OCH2C°CH | CF3 | Br | 2-methyl-2H-tetrazol-5-yl | |
| 264 | OCH2CH3 | CF3 | I | 1,2,4-triazol-1-yl | |
| 265 | OCH2CH3 | CF2CF3 | I | 1,2,4-triazol-1-yl | |
| 266 | OCH2CH3 | CF3 | I | 2H-tetrazol-5-yl | |
| 267 | OCH2CH3 | CF2CF3 | I | 2H-tetrazol-5-yl | |
| 268 | OCH2CH3 | CF3 | I | 2-methyl-2H-tetrazol-5-yl | |
| 269 | OCH2CH3 | CF2CF3 | I | 2-methyl-2H-tetrazol-5-yl | |
| 270 | OCH2CH3 | CF3 | I | 4-methylimidazol-1-yl | |
| 271 | OCH2CH3 | CF2CF3 | I | 4-methylimidazol-1-yl | |
| 272 | OCH2CH3 | CF3 | I | benzimidazol-1-yl | |
| 273 | OCH2CH3 | CF2CF3 | I | benzimidazol-1-yl | |
| 274 | OCH2CH3 | CF3 | I | imidazol-1-yl | 103–105 |
| 275 | OCH2CH3 | CF2CF3 | I | imidazol-1-yl | |
| 276 | OCH2CH3 | CF3 | F | 2H-tetrazol-5-yl | |
| 277 | OCH2CH3 | CF3 | F | 2-methyl-2H-tetrazol-5-yl | |
| 278 | OCH2CH3 | CF3 | Cl | 2H-tetrazol-5-yl | |
| 279 | OCH2CH3 | CF3 | Cl | 2-methyl-2H-tetrazol-5-yl | |
| 280 | OCH2CH3 | CF3 | Br | 2H-tetrazol-5-yl | |
| 281 | OCH2CH3 | CF3 | Br | 2-methyl-2H-tetrazol-5-yl | |
| 282 | OCH2CH2CH3 | CF3 | I | 1,2,4-triazol-1-yl | |
| 283 | OCH2CH2CH3 | CF2CF3 | I | 1,2,4-triazol-1-yl | |
| 284 | OCH2CH2CH3 | CF3 | I | 2H-tetrazol-5-yl | |
| 285 | OCH2CH2CH3 | CF2CF3 | I | 2H-tetrazol-5-yl | |

TABLE 1-continued $$\text{(1)}$$

Structure: pyrimidine with Q at 4-position, R¹ at 2-position, R² at 6-position, R³ at 5-position.

| No. | R1 | R2 | R3 | Q | mp (° C.) |
|---|---|---|---|---|---|
| 286 | OCH2CH2CH3 | CF3 | I | 2-methyl-2H-tetrazol-5-yl | |
| 287 | OCH2CH2CH3 | CF2CF3 | I | 2-methyl-2H-tetrazol-5-yl | |
| 288 | OCH2CH2CH3 | CF3 | I | 4-methylimidazol-1-yl | |
| 289 | OCH2CH2CH3 | CF2CF3 | I | 4-methylimidazol-1-yl | |
| 290 | OCH2CH2CH3 | CF3 | I | benzimidazol-1-yl | |
| 291 | OCH2CH2CH3 | CF2CF3 | I | benzimidazol-1-yl | |
| 292 | OCH2CH2CH3 | CF3 | I | imidazol-1-yl | 84–86 |
| 293 | OCH2CH2CH3 | CF2CF3 | I | imidazol-1-yl | |
| 294 | OCH2CH2CH3 | CF3 | F | 2H-tetrazol-5-yl | |
| 295 | OCH2CH2CH3 | CF3 | F | 2-methyl-2H-tetrazol-5-yl | |
| 296 | OCH2CH2CH3 | CF3 | Cl | 2H-tetrazol-5-yl | |
| 297 | OCH2CH2CH3 | CF3 | Cl | 2-methyl-2H-tetrazol-5-yl | |
| 298 | OCH2CH2CH3 | CF3 | Br | 2H-tetrazol-5-yl | |
| 299 | OCH2CH2CH3 | CF3 | Br | 2-methyl-2H-tetrazol-5-yl | |
| 300 | OCH2CF2H | CF3 | I | 1,2,4-triazol-1-yl | |
| 301 | OCH2CF2H | CF2CF3 | I | 1,2,4-triazol-1-yl | |
| 302 | OCH2CF2H | CF3 | I | 2H-tetrazol-5-yl | |
| 303 | OCH2CF2H | CF2CF3 | I | 2H-tetrazol-5-yl | |
| 304 | OCH2CF2H | CF3 | I | 2-methyl-2H-tetrazol-5-yl | |
| 305 | OCH2CF2H | CF2CF3 | I | 2-methyl-2H-tetrazol-5-yl | |
| 306 | OCH2CF2H | CF3 | I | 4-methylimidazol-1-yl | |
| 307 | OCH2CF2H | CF2CF3 | I | 4-methylimidazol-1-yl | |
| 308 | OCH2CF2H | CF3 | I | benzimidazol-1-yl | |
| 309 | OCH2CF2H | CF2CF3 | I | benzimidazol-1-yl | |
| 310 | OCH2CF2H | CF3 | I | imidazol-1-yl | 97–98 |
| 311 | OCH2CF2H | CF2CF3 | I | imidazol-1-yl | |
| 312 | OCH2CF2H | CF3 | F | 2H-tetrazol-5-yl | |
| 313 | OCH2CF2H | CF3 | F | 2-methyl-2H-tetrazol-5-yl | |
| 314 | OCH2CF2H | CF3 | Cl | 2H-tetrazol-5-yl | |
| 315 | OCH2CF2H | CF3 | Cl | 2-methyl-2H-tetrazol-5-yl | |
| 316 | OCH2CF2H | CF3 | Br | 2H-tetrazol-5-yl | |
| 317 | OCH2CF2H | CF3 | Br | 2-methyl-2H-tetrazol-5-yl | |
| 318 | OCH(CH3)2 | CF3 | I | 1,2,4-triazol-1-yl | |
| 319 | OCH(CH3)2 | CF2CF3 | I | 1,2,4-triazol-1-yl | |
| 320 | OCH(CH3)2 | CF3 | I | 2H-tetrazol-5-yl | |
| 321 | OCH(CH3)2 | CF2CF3 | I | 2H-tetrazol-5-yl | |
| 322 | OCH(CH3)2 | CF3 | I | 2-methyl-2H-tetrazol-5-yl | |
| 323 | OCH(CH3)2 | CF2CF3 | I | 2-methyl-2H-tetrazol-5-yl | |
| 324 | OCH(CH3)2 | CF3 | I | 4-methylimidazol-1-yl | |
| 325 | OCH(CH3)2 | CF2CF3 | I | 4-methylimidazol-1-yl | |
| 326 | OCH(CH3)2 | CF3 | I | benzimidazol-1-yl | |
| 327 | OCH(CH3)2 | CF2CF3 | I | benzimidazol-1-yl | |
| 328 | OCH(CH3)2 | CF3 | I | imidazol-1-yl | 97–98 |
| 329 | OCH(CH3)2 | CF2CF3 | I | imidazol-1-yl | |
| 330 | OCH(CH3)2 | CF3 | F | 2H-tetrazol-5-yl | |
| 331 | OCH(CH3)2 | CF3 | F | 2-methyl-2H-tetrazol-5-yl | |
| 332 | OCH(CH3)2 | CF3 | Cl | 2H-tetrazol-5-yl | |
| 333 | OCH(CH3)2 | CF3 | Cl | 2-methyl-2H-tetrazol-5-yl | |
| 334 | OCH(CH3)2 | CF3 | Br | 2H-tetrazol-5-yl | |
| 335 | OCH(CH3)2 | CF3 | Br | 2-methyl-2H-tetrazol-5-yl | |
| 336 | imidazol-1-yl | CF3 | I | 1,2,4-triazol-1-yl | |
| 337 | imidazol-1-yl | CF2CF3 | I | 1,2,4-triazol-1-yl | |
| 338 | imidazol-1-yl | CF3 | I | 2H-tetrazol-5-yl | |
| 339 | imidazol-1-yl | CF2CF3 | I | 2H-tetrazol-5-yl | |
| 340 | imidazol-1-yl | CF3 | I | 2-methyl-2H-tetrazol-5-yl | |
| 341 | imidazol-1-yl | CF2CF3 | I | 2-methyl-2H-tetrazol-5-yl | |
| 342 | imidazol-1-yl | CF3 | I | 4-methylimidazol-1-yl | |
| 343 | imidazol-1-yl | CF2CF3 | I | 4-methylimidazol-1-yl | |
| 344 | imidazol-1-yl | CF3 | I | benzimidazol-1-yl | |
| 345 | imidazol-1-yl | CF2CF3 | I | benzimidazol-1-yl | |
| 346 | imidazol-1-yl | CF3 | I | imidazol-1-yl | >160 dec |
| 347 | imidazol-1-yl | CF2CF3 | I | imidazol-1-yl | |
| 348 | imidazol-1-yl | CF3 | F | 2H-tetrazol-5-yl | |
| 349 | imidazol-1-yl | CF3 | F | 2-methyl-2H-tetrazol-5-yl | |
| 350 | imidazol-1-yl | CF3 | F | imidazol-1-yl | 142–150 dec |

TABLE 1-continued $$\text{(1)}$$

Structure: pyrimidine with Q at 4-position, R1 at 2-position, R2 at 6-position, R3 at 5-position.

| No. | R1 | R2 | R3 | Q | mp (° C.) |
|---|---|---|---|---|---|
| 351 | imidazol-1-yl | CF3 | Cl | 2H-tetrazol-5-yl | |
| 352 | imidazol-1-yl | CF3 | Cl | 2-methyl-2H-tetrazol-5-yl | |
| 353 | imidazol-1-yl | CF3 | Br | 2H-tetrazol-5-yl | |
| 354 | imidazol-1-yl | CF3 | Br | 2-methyl-2H-tetrazol-5-yl | |
| 355 | H | CF3 | I | 1,2,4-triazol-1-yl | 115–116 |
| 356 | H | CF2CF3 | I | 1,2,4-triazol-1-yl | |
| 357 | H | CF3 | I | 2H-tetrazol-5-yl | |
| 358 | H | CF2CF3 | I | 2H-tetrazol-5-yl | |
| 359 | H | CF3 | I | 2-methyl-2H-tetrazol-5-yl | |
| 360 | H | CF2CF3 | I | 2-methyl-2H-tetrazol-5-yl | |
| 361 | H | CF3 | I | 3-(p-acetoxybenzylthio)-1,2,4-triazol-1-yl | |
| 362 | H | CF3 | I | 3-amino-1,2,4-triazol-1-yl | |
| 363 | H | CF3 | I | 3-bromo-1,2,4-triazol-1-yl | |
| 364 | H | CF3 | I | 3-chloro-1,2,4-triazol-1-yl | |
| 365 | H | CF3 | I | 3-cyano-1,2,4-triazol-1-yl | |
| 366 | H | CF3 | I | 3-fluoro-1,2,4-triazol-1-yl | |
| 367 | H | CF3 | I | 3-hydroxy-1,2,4-triazol-1-yl | |
| 368 | H | CF3 | I | 3-mercapto-1,2,4-triazol-1-yl | |
| 369 | H | CF3 | I | 3-methoxy-1,2,4-triazol-1-yl | |
| 370 | H | CF3 | I | 3-methylamino-1,2,4-triazol-1-yl | |
| 371 | H | CF3 | I | 3-methylthio-1,2,4-triazol-1-yl | |
| 372 | H | CF3 | I | 3-trifluoromethyl-1,2,4-triazol-1-yl | |
| 373 | H | CF3 | I | 5-(p-acetoxybenzylthio)imidazol-1-yl | |
| 374 | H | CF3 | I | 5-(p-acetoxybenzylthio)-1,2,4-triazol-1-yl | |
| 375 | H | CF3 | I | 4-aminoimidazol-1-yl | |
| 376 | H | CF3 | I | 5-amino-1,2,4-triazol-1-yl | |
| 377 | H | CF3 | I | 4-bromoimidazol-1-yl | |
| 378 | H | CF3 | I | 5-bromo-1,2,4-triazol-1-yl | |
| 379 | H | CF3 | I | 4-chloroimidazol-1-yl | |
| 380 | H | CF3 | I | 5-chloro-1,2,4-triazol-1-yl | |
| 381 | H | CF3 | I | 4-cyanoimidazol-1-yl | |
| 382 | H | CF3 | I | 5-cyano-1,2,4-triazol-1-yl | |
| 383 | H | CF3 | I | 4-fluoroimidazol-1-yl | |
| 384 | H | CF3 | I | 5-fluoro-1,2,4-triazol-1-yl | |
| 385 | H | CF3 | I | 4-hydroxyimidazol-1-yl | |
| 386 | H | CF3 | I | 5-hydroxy-1,2,4-triazol-1-yl | |
| 387 | H | CF3 | I | 4-mercaptoimidazol-1-yl | |
| 388 | H | CF3 | I | 5-mercapto-1,2,4-triazol-1-yl | |
| 389 | H | CF3 | I | 4-methoxyimidazol-1-yl | |
| 390 | H | CF3 | I | 5-methoxy-1,2,4-triazol-1-yl | |
| 391 | H | CF3 | I | 4-methylaminoimidazol-1-yl | |
| 392 | H | CF3 | I | 5-methylamino-1,2,4-triazol-1-yl | |
| 393 | H | CF3 | I | 4-methylimidazol-1-yl | 173–175 |
| 394 | H | CF2CF3 | I | 4-methylimidazol-1-yl | |
| 395 | H | CF3 | I | 4-methylthioimidazol-1-yl | |
| 396 | H | CF3 | I | 5-methylthio-1,2,4-triazol-1-yl | |
| 397 | H | CF3 | I | 4-trifluoromethylimidazol-1-yl | |
| 398 | H | CF3 | I | 5-trifluoromethyl-1,2,4-triazol-1-yl | |
| 399 | H | CF3 | I | benzimidazol-1-yl | 119–120 |
| 400 | H | CF2CF3 | I | benzimidazol-1-yl | |
| 401 | H | CF3 | I | imidazol-1-yl | 108–109 |
| 402 | H | CF2CF3 | I | imidazol-1-yl | |
| 403 | H | CF3 | F | 2H-tetrazol-5-yl | |
| 404 | H | CF3 | F | 2-methyl-2H-tetrazol-5-yl | |
| 405 | H | CF3 | Cl | 2H-tetrazol-5-yl | |
| 406 | H | CF3 | Cl | 2-methyl-2H-tetrazol-5-yl | |
| 407 | H | CF3 | Br | 2H-tetrazol-5-yl | |
| 408 | H | CF3 | Br | 2-methyl-2H-tetrazol-5-yl | |
| 409 | C°CSi(CH3)3 | CF3 | I | 1,2,4-triazol-1-yl | |
| 410 | C°CSi(CH3)3 | CF2CF3 | I | 1,2,4-triazol-1-yl | |
| 411 | C°CSi(CH3)3 | CF3 | I | 2H-tetrazol-5-yl | |
| 412 | C°CSi(CH3)3 | CF2CF3 | I | 2H-tetrazol-5-yl | |
| 413 | C°CSi(CH3)3 | CF3 | I | 2-methyl-2H-tetrazol-5-yl | |
| 414 | C°CSi(CH3)3 | CF2CF3 | I | 2-methyl-2H-tetrazol-5-yl | |
| 415 | C°CSi(CH3)3 | CF3 | I | 4-methylimidazol-1-yl | |
| 416 | C°CSi(CH3)3 | CF2CF3 | I | 4-methylimidazol-1-yl | |
| 417 | C°CSi(CH3)3 | CF3 | I | benzimidazol-1-yl | |

TABLE 1-continued (1)

| No. | R1 | R2 | R3 | Q | mp (° C.) |
|---|---|---|---|---|---|
| 418 | C≡CSi(CH3)3 | CF2CF3 | I | benzimidazol-1-yl | |
| 419 | C≡CSi(CH3)3 | CF3 | I | imidazol-1-yl | oil |
| 420 | C≡CSi(CH3)3 | CF2CF3 | I | imidazol-1-yl | |
| 421 | C≡CSi(CH3)3 | CF3 | F | 2H-tetrazol-5-yl | |
| 422 | C≡CSi(CH3)3 | CF3 | F | 2-methyl-2H-tetrazol-5-yl | |
| 423 | C≡CSi(CH3)3 | CF3 | Cl | 2H-tetrazol-5-yl | |
| 424 | C≡CSi(CH3)3 | CF3 | Cl | 2-methyl-2H-tetrazol-5-yl | |
| 425 | C≡CSi(CH3)3 | CF3 | Br | 2H-tetrazol-5-yl | |
| 426 | C≡CSi(CH3)3 | CF3 | Br | 2-methyl-2H-tetrazol-5-yl | |
| 427 | CH3 | CF3 | vinyl | imidazol-1-yl | oil |
| 428 | CH3 | CF3 | I | 1,2,4-triazol-1-yl | 119–121 |
| 429 | CH3 | CF2CF3 | I | 1,2,4-triazol-1-yl | |
| 430 | CH3 | CF3 | I | 2H-tetrazol-5-yl | 180–182 |
| 431 | CH3 | CF2CF3 | I | 2H-tetrazol-5-yl | |
| 432 | CH3 | CF3 | I | 2-methyl-2H-tetrazol-5-yl | 131–133 |
| 433 | CH3 | CF2CF3 | I | 2-methyl-2H-tetrazol-5-yl | |
| 434 | CH3 | CF3 | I | 3-(p-acetoxybenzylthio)-1,2,4-triazol-1-yl | |
| 435 | CH3 | CF3 | I | 3-amino-1,2,4-triazol-1-yl | |
| 436 | CH3 | CF3 | I | 3-bromo-1,2,4-triazol-1-yl | |
| 437 | CH3 | CF3 | I | 3-chloro-1,2,4-triazol-1-yl | |
| 438 | CH3 | CF3 | I | 3-cyano-1,2,4-triazol-1-yl | |
| 439 | CH3 | CF3 | I | 3-fluoro-1,2,4-triazol-1-yl | |
| 440 | CH3 | CF3 | I | 3-hydroxy-1,2,4-triazol-1-yl | |
| 441 | CH3 | CF3 | I | 3-mercapto-1,2,4-triazol-1-yl | |
| 442 | CH3 | CF3 | I | 3-methoxy-1,2,4-triazol-1-yl | |
| 443 | CH3 | CF3 | I | 3-methylamino-1,2,4-triazol-1-yl | |
| 444 | CH3 | CF3 | I | 3-methylthio-1,2,4-triazol-1-yl | |
| 445 | CH3 | CF3 | I | 3-trifluoromethyl-1,2,4-triazol-1-yl | |
| 446 | CH3 | CF3 | I | 5-(p-acetoxybenzylthio)imidazol-1-yl | |
| 447 | CH3 | CF3 | I | 5-(p-acetoxybenzylthio)-1,2,4-triazol-1-yl | |
| 448 | CH3 | CF3 | I | 4-aminoimidazol-1-yl | |
| 449 | CH3 | CF3 | I | 5-amino-1,2,4-triazol-1-yl | |
| 450 | CH3 | CF3 | I | 4-bromoimidazol-1-yl | |
| 451 | CH3 | CF3 | I | 5-bromo-1,2,4-triazol-1-yl | |
| 452 | CH3 | CF3 | I | 4-chloroimidazol-1-yl | |
| 453 | CH3 | CF3 | I | 5-chloro-1,2,4-triazol-1-yl | |
| 454 | CH3 | CF3 | I | 4-cyanoimidazol-1-yl | |
| 455 | CH3 | CF3 | I | 5-cyano-1,2,4-triazol-1-yl | |
| 456 | CH3 | CF3 | I | 4-fluoroimidazol-1-yl | |
| 457 | CH3 | CF3 | I | 5-fluoro-1,2,4-triazol-1-yl | |
| 458 | CH3 | CF3 | I | 4-hydroxyimidazol-1-yl | |
| 459 | CH3 | CF3 | I | 5-hydroxy-1,2,4-triazol-1-yl | |
| 460 | CH3 | CF3 | I | 4-mercaptoimidazol-1-yl | |
| 461 | CH3 | CF3 | I | 5-mercapto-1,2,4-triazol-1-yl | |
| 462 | CH3 | CF3 | I | 4-methoxyimidazol-1-yl | |
| 463 | CH3 | CF3 | I | 5-methoxy-1,2,4-triazol-1-yl | |
| 464 | CH3 | CF3 | I | 4-methylaminoimidazol-1-yl | |
| 465 | CH3 | CF3 | I | 5-methylamino-1,2,4-triazol-1-yl | |
| 466 | CH3 | CF3 | I | 4-methylimidazol-1-yl | 155–156 |
| 467 | CH3 | CF2CF3 | I | 4-methylimidazol-1-yl | |
| 468 | CH3 | CF3 | I | 4-methylthioimidazol-1-yl | |
| 469 | CH3 | CF3 | I | 5-methylthio-1,2,4-triazol-1-yl | |
| 470 | CH3 | CF3 | I | 4-trifluoromethylimidazol-1-yl | |
| 471 | CH3 | CF3 | I | 5-trifluoromethyl-1,2,4-triazol-1-yl | |
| 472 | CH3 | CF3 | I | benzimidazol-1-yl | |
| 473 | CH3 | CF2CF3 | I | benzimidazol-1-yl | |
| 474 | CH3 | CF3 | I | imidazol-1-yl | 145–148 |
| 475 | CH3 | CF2CF3 | I | imidazol-1-yl | |
| 476 | CH3 | CF3 | F | 2H-tetrazol-5-yl | |
| 477 | CH3 | CF3 | F | 2-methyl-2H-tetrazol-5-yl | |
| 478 | CH3 | CF3 | ethynyl | imidazol-1-yl | 121–122 |
| 479 | CH3 | CF3 | Cl | 2H-tetrazol-5-yl | |
| 480 | CH3 | CF3 | Cl | 2-methyl-2H-tetrazol-5-yl | |
| 481 | CH3 | CF3 | Br | 2H-tetrazol-5-yl | |
| 482 | CH3 | CF3 | Br | 2-methyl-2H-tetrazol-5-yl | |
| 483 | CH3 | CF3 | Br | imidazol-1-yl | 72–73 |

TABLE 1-continued (1)

| No. | R1 | R2 | R3 | Q | mp (° C.) |
|---|---|---|---|---|---|
| 484 | CH3 | CF3 | 1-chloro-vinyl | imidazol-1-yl | oil |
| 485 | CH2CH3 | CF3 | I | 1,2,4-triazol-1-yl | 50–51 |
| 486 | CH2CH3 | CF2CF3 | I | 1,2,4-triazol-1-yl | |
| 487 | CH2CH3 | CF3 | I | 2H-tetrazol-5-yl | |
| 488 | CH2CH3 | CF2CF3 | I | 2H-tetrazol-5-yl | |
| 489 | CH2CH3 | CF3 | I | 2-methyl-2H-tetrazol-5-yl | |
| 490 | CR2CH3 | CF2CF3 | I | 2-methyl-2H-tetrazol-5-yl | |
| 491 | CH2CH3 | CF3 | I | 3-(p-acetoxybenzylthio)-1,2,4-triazol-1-yl | |
| 492 | CH2CH3 | CF3 | I | 3-amino-1,2,4-triazol-1-yl | |
| 493 | CH2CH3 | CF3 | I | 3-bromo-1,2,4-triazol-1-yl | |
| 494 | CH2CH3 | CF3 | I | 3-chloro-1,2,4-triazol-1-yl | |
| 495 | CH2CH3 | CF3 | I | 3-cyano-1,2,4-triazol-1-yl | |
| 496 | CH2CH3 | CF3 | I | 3-fluoro-1,2,4-triazol-1-yl | |
| 497 | CH2CH3 | CF3 | I | 3-hydroxy-1,2,4-triazol-1-yl | |
| 498 | CH2CH3 | CF3 | I | 3-mercapto-1,2,4-triazol-1-yl | |
| 499 | CH2CH3 | CF3 | I | 3-methoxy-1,2,4-triazol-1-yl | |
| 500 | CH2CH3 | CF3 | I | 3-methylamino-1,2,4-triazol-1-yl | |
| 501 | CH2CH3 | CF3 | I | 3-methylthio-1,2,4-triazol-1-yl | |
| 502 | CH2CH3 | CF3 | I | 3-trifluoromethyl-1,2,4-triazol-1-yl | |
| 503 | CH2CH3 | CF3 | I | 5-(p-acetoxybenzylthio)imidazol-1-yl | |
| 504 | CH2CH3 | CF3 | I | 5-(p-acetoxybenzylthio)-1,2,4-triazol-1-yl | |
| 505 | CH2CH3 | CF3 | I | 4-aminoimidazol-1-yl | |
| 506 | CH2CH3 | CF3 | I | 5-amino-1,2,4-triazol-1-yl | |
| 507 | CH2CH3 | CF3 | I | 4-bromoimidazol-1-yl | |
| 508 | CH2CH3 | CF3 | I | 5-bromo-1,2,4-triazol-1-yl | |
| 509 | CH2CH3 | CF3 | I | 4-chloroimidazol-1-yl | |
| 510 | CH2CH3 | CF3 | I | 5-chloro-1,2,4-triazol-1-yl | |
| 511 | CH2CH3 | CF3 | I | 4-cyanoimidazol-1-yl | |
| 512 | CH2CH3 | CF3 | I | 5-cyano-1,2,4-triazol-1-yl | |
| 513 | CH2CH3 | CF3 | I | 4-fluoroimidazol-1-yl | |
| 514 | CH2CH3 | CF3 | I | 5-fluoro-1,2,4-triazol-1-yl | |
| 515 | CH2CH3 | CF3 | I | 4-hydroxyimidazol-1-yl | |
| 516 | CH2CH3 | CF3 | I | 5-hydroxy-1,2,4-triazol-1-yl | |
| 517 | CH2CH3 | CF3 | I | 4-mercaptoimidazol-1-yl | |
| 518 | CH2CH3 | CF3 | I | 5-mercapto-1,2,4-triazol-1-yl | |
| 519 | CH2CH3 | CF3 | I | 4-methoxyimidazol-1-yl | |
| 520 | CH2CH3 | CF3 | I | 5-methoxy-1,2,4-triazol-1-yl | |
| 521 | CH2CH3 | CF3 | I | 4-methylaminoimidazol-1-yl | |
| 522 | CH2CH3 | CF3 | I | 5-methylamino-1,2,4-triazol-1-yl | |
| 523 | CH2CH3 | CF3 | I | 4-methylimidazol-1-yl | 110–111 |
| 524 | CH2CH3 | CF2CF3 | I | 4-methylimidazol-1-yl | |
| 525 | CH2CH3 | CF3 | I | 4-methylthioimidazol-1-yl | |
| 526 | CH2CH3 | CF3 | I | 5-methylthio-1,2,4-triazol-1-yl | |
| 527 | CH2CH3 | CF3 | I | 4-trifluoromethylimidazol-1-yl | |
| 528 | CH2CH3 | CF3 | I | 5-trifluoromethyl-1,2,4-triazol-1-yl | |
| 529 | CH2CH3 | CF3 | I | benzimidazol-1-yl | |
| 530 | CH2CH3 | CF2CF3 | I | benzimidazol-1-yl | |
| 531 | CH2CH3 | CF3 | I | imidazol-1-yl | 124 |
| 532 | CH2CH3 | CF2CF3 | I | imidazol-1-yl | |
| 533 | CH2CH3 | CF3 | F | 2H-tetrazol-5-yl | |
| 534 | CH2CH3 | CF3 | F | 2-methyl-2H-tetrazol-5-yl | |
| 535 | CH2CH3 | CF3 | Cl | 2H-tetrazol-5-yl | |
| 536 | CH2CH3 | CF3 | Cl | 2-methyl-2H-tetrazol-5-yl | |
| 537 | CH2CH3 | CF3 | Br | 2H-tetrazol-5-yl | |
| 538 | CH2CH3 | CF3 | Br | 2-methyl-2H-tetrazol-5-yl | |
| 539 | 6-phenylpiridin-2-yl | CF3 | I | 1,2,4-triazol-1-yl | |
| 540 | 6-phenylpiridin-2-yl | CF2CF3 | I | 1,2,4-triazol-1-yl | |
| 541 | 6-phenylpiridin-2-yl | CF3 | I | 2H-tetrazol-5-yl | |
| 542 | 6-phenylpiridin-2-yl | CF2CF3 | I | 2H-tetrazol-5-yl | |
| 543 | 6-phenylpiridin-2-yl | CF3 | I | 2-methyl-2H-tetrazol-5-yl | |
| 544 | 6-phenylpiridin-2-yl | CF2CF3 | I | 2-methyl-2H-tetrazol-5-yl | |
| 545 | 6-phenylpiridin-2-yl | CF3 | I | 4-methylimidazol-1-yl | |
| 546 | 6-phenylpiridin-2-yl | CF2CF3 | I | 4-methylimidazol-1-yl | |
| 547 | 6-phenylpiridin-2-yl | CF3 | I | benzimidzol-1-yl | |
| 548 | 6-phenylpiridin-2-yl | CF2CF3 | I | benzimidzol-1-yl | |
| 549 | 6-phenylpiridin-2-yl | CF3 | I | imidazol-1-yl | |

TABLE 1-continued structure (1): pyrimidine with Q at 4-position, R¹ at 2-position, R² at 6-position, R³ at 5-position

| No. | R1 | R2 | R3 | Q | mp (° C.) |
|---|---|---|---|---|---|
| 550 | 6-phenylpiridin-2-yl | CF2CF3 | I | imidazol-1-yl | |
| 551 | 6-phenylpiridin-2-yl | CF3 | F | 2H-tetrazol-5-yl | |
| 552 | 6-phenylpiridin-2-yl | CF3 | F | 2-methyl-2H-tetrazol-5-yl | |
| 553 | 6-phenylpiridin-2-yl | CF3 | Cl | 2H-tetrazol-5-yl | |
| 554 | 6-phenylpiridin-2-yl | CF3 | Cl | 2-methyl-2H-tetrazol-5-yl | |
| 555 | 6-phenylpiridin-2-yl | CF3 | Br | 2H-tetrazol-5-yl | |
| 556 | 6-phenylpiridin-2-yl | CF3 | Br | 2-methyl-2H-tetrazol-5-yl | |
| 557 | 6-phenylpiridin-2-yl | CF3 | Br | imidazol-1-yl | 136–138 |
| 558 | 6-methylpiridin-2-yl | CF3 | I | 1,2,4-triazol-1-yl | |
| 559 | 6-methylpiridin-2-yl | CF2CF3 | I | 1,2,4-triazol-1-yl | |
| 560 | 6-methylpiridin-2-yl | CF3 | I | 2H-tetrazol-5-yl | |
| 561 | 6-methylpiridin-2-yl | CF2CF3 | I | 2H-tetrazol-5-yl | |
| 562 | 6-methylpiridin-2-yl | CF3 | I | 2-methyl-2H-tetrazol-5-yl | |
| 563 | 6-methylpiridin-2-yl | CF2CF3 | I | 2-methyl-2H-tetrazol-5-yl | |
| 564 | 6-methylpiridin-2-yl | CF3 | I | 4-methylimidazol-1-yl | |
| 565 | 6-methylpiridin-2-yl | CF2CF3 | I | 4-methylimidazol-1-yl | |
| 566 | 6-methylpiridin-2-yl | CF3 | I | benzimidzol-1-yl | |
| 567 | 6-methylpiridin-2-yl | CF2CF3 | I | benzimidzol-1-yl | |
| 568 | 6-methylpiridin-2-yl | CF3 | I | imidazol-1-yl | 141–143 |
| 569 | 6-methylpiridin-2-yl | CF2CF3 | I | imidazol-1-yl | |
| 570 | 6-methylpiridin-2-yl | CF3 | F | 2H-tetrazol-5-yl | |
| 571 | 6-methylpiridin-2-yl | CF3 | F | 2-methyl-2H-tetrazol-5-yl | |
| 572 | 6-methylpiridin-2-yl | CF3 | Cl | 2H-tetrazol-5-yl | |
| 573 | 6-methylpiridin-2-yl | CF3 | Cl | 2-methyl-2H-tetrazol-5-yl | |
| 574 | 6-methylpiridin-2-yl | CF3 | Br | 2H-tetrazol-5-yl | |
| 575 | 6-methylpiridin-2-yl | CF3 | Br | 2-methyl-2H-tetrazol-5-yl | |
| 576 | 2-oxopyrrolidin-1-yl | CF3 | I | 1,2,4-triazol-1-yl | |
| 577 | 2-oxopyrrolidin-1-yl | CF2CF3 | I | 1,2,4-triazol-1-yl | |
| 578 | 2-oxopyrrolidin-1-yl | CF3 | I | 2H-tetrazol-5-yl | |
| 579 | 2-oxopyrrolidin-1-yl | CF2CF3 | I | 2H-tetrazol-5-yl | |
| 580 | 2-oxopyrrolidin-1-yl | CF3 | I | 2-methyl-2H-tetrazol-5-yl | |
| 581 | 2-oxopyrrolidin-1-yl | CF2CF3 | I | 2-methyl-2H-tetrazol-5-yl | |
| 582 | 2-oxopyrrolidin-1-yl | CF3 | I | 4-methylimidazol-1-yl | |
| 583 | 2-oxopyrrolidin-1-yl | CF2CF3 | I | 4-methylimidazol-1-yl | |
| 584 | 2-oxopyrrolidin-1-yl | CF3 | I | benzimidzol-1-yl | |
| 585 | 2-oxopyrrolidin-1-yl | CF2CF3 | I | benzimidzol-1-yl | |
| 586 | 2-oxopyrrolidin-1-yl | CF3 | I | imidazol-1-yl | 195–197 |
| 587 | 2-oxopyrrolidin-1-yl | CF2CF3 | I | imidazol-1-yl | |
| 588 | 2-oxopyrrolidin-1-yl | CF3 | F | 2H-tetrazol-5-yl | |
| 589 | 2-oxopyrrolidin-1-yl | CF3 | F | 2-methyl-2H-tetrazol-5-yl | |
| 590 | 2-oxopyrrolidin-1-yl | CF3 | Cl | 2H-tetrazol-5-yl | |
| 591 | 2-oxopyrrolidin-1-yl | CF3 | Cl | 2-methyl-2H-tetrazol-5-yl | |
| 592 | 2-oxopyrrolidin-1-yl | CF3 | Br | 2H-tetrazol-5-yl | |
| 593 | 2-oxopyrrolidin-1-yl | CF3 | Br | 2-methyl-2H-tetrazol-5-yl | |
| 594 | CH3 | CF3 | I | 1-methyl-1H-tetrazol-5-yl | 110–112 |
| 595 | SCH3 | CF3 | I | 1-methyl-1H-tetrazol-5-yl | |
| 596 | SCH2CH3 | CF3 | I | 1-methyl-1H-tetrazol-5-yl | |
| 597 | OCH3 | CF3 | I | 1-methyl-1H-tetrazol-5-yl | |
| 598 | OCH2CH3 | CF3 | I | 1-methyl-1H-tetrazol-5-yl | |
| 599 | H | CF3 | I | 1-methyl-1H-tetrazol-5-yl | |
| 600 | CH2CH3 | CF3 | I | 1-methyl-1H-tetrazol-5-yl | |
| 601 | phenyl | CF3 | I | 1-methyl-1H-tetrazol-5-yl | |
| 602 | imidazol-1-yl | CF3 | I | 1-methyl-1H-tetrazol-5-yl | |
| 603 | pyridin-2-yl | CF3 | I | 1-methyl-1H-tetrazol-5-yl | |
| 604 | pyridin-3-yl | CF3 | I | 1-methyl-1H-tetrazol-5-yl | |
| 605 | pyridin-4-yl | CF3 | I | 1-methyl-1H-tetrazol-5-yl | |
| 606 | CH3 | CF3 | Br | 1-methyl-1H-tetrazol-5-yl | |
| 607 | SCH3 | CF3 | Br | 1-methyl-1H-tetrazol-5-yl | |
| 608 | SCH2CH3 | CF3 | Br | 1-methyl-1H-tetrazol-5-yl | |
| 609 | OCH3 | CF3 | Br | 1-methyl-1H-tetrazol-5-yl | |
| 610 | OCH2CH3 | CF3 | Br | 1-methyl-1H-tetrazol-5-yl | |
| 611 | H | CF3 | Br | 1-methyl-1H-tetrazol-5-yl | |
| 612 | CH2CH3 | CF3 | Br | 1-methyl-1H-tetrazol-5-yl | |
| 613 | phenyl | CF3 | Br | 1-methyl-1H-tetrazol-5-yl | |
| 614 | imidazol-1-yl | CF3 | Br | 1-methyl-1H-tetrazol-5-yl | |
| 615 | pyridin-2-yl | CF3 | Br | 1-methyl-1H-tetrazol-5-yl | |
| 616 | pyridin-3-yl | CF3 | Br | 1-methyl-1H-tetrazol-5-yl | |

TABLE 1-continued

Structure (1): pyrimidine with Q at 4-position, R¹ at 2-position, R² at 6-position, R³ at 5-position.

| No. | R1 | R2 | R3 | Q | mp (° C.) |
|---|---|---|---|---|---|
| 617 | pyridin-4-yl | CF3 | Br | 1-methyl-1H-tetrazol-5-yl | |
| 618 | CH3 | CF3 | Cl | 1-methyl-1H-tetrazol-5-yl | |
| 619 | SCH3 | CF3 | Cl | 1-methyl-1H-tetrazol-5-yl | |
| 620 | SCH2CH3 | CF3 | Cl | 1-methyl-1H-tetrazol-5-yl | |
| 621 | OCH3 | CF3 | Cl | 1-methyl-1H-tetrazol-5-yl | |
| 622 | OCH2CH3 | CF3 | Cl | 1-methyl-1H-tetrazol-5-yl | |
| 623 | H | CF3 | Cl | 1-methyl-1H-tetrazol-5-yl | |
| 624 | CH2CH3 | CF3 | Cl | 1-methyl-1H-tetrazol-5-yl | |
| 625 | phenyl | CF3 | Cl | 1-methyl-1H-tetrazol-5-yl | |
| 626 | imidazol-1-yl | CF3 | Cl | 1-methyl-1H-tetrazol-5-yl | |
| 627 | pyridin-2-yl | CF3 | Cl | 1-methyl-1H-tetrazol-5-yl | |
| 628 | pyridin-3-yl | CF3 | Cl | 1-methyl-1H-tetrazol-5-yl | |
| 629 | pyridin-4-yl | CF3 | Cl | 1-methyl-1H-tetrazol-5-yl | |
| 630 | CH3 | CF3 | F | 1-methyl-1H-tetrazol-5-yl | |
| 631 | SCH3 | CF3 | F | 1-methyl-1H-tetrazol-5-yl | |
| 632 | SCH2CH3 | CF3 | F | 1-methyl-1H-tetrazol-5-yl | |
| 633 | OCH3 | CF3 | F | 1-methyl-1H-tetrazol-5-yl | |
| 634 | OCH2CH3 | CF3 | F | 1-methyl-1H-tetrazol-5-yl | |
| 635 | H | CF3 | F | 1-methyl-1H-tetrazol-5-yl | |
| 636 | CH2CH3 | CF3 | F | 1-methyl-1H-tetrazol-5-yl | |
| 637 | phenyl | CF3 | F | 1-methyl-1H-tetrazol-5-yl | |
| 638 | imidazol-1-yl | CF3 | F | 1-methyl-1H-tetrazol-5-yl | |
| 639 | pyridin-2-yl | CF3 | F | 1-methyl-1H-tetrazol-5-yl | |
| 640 | pyridin-3-yl | CF3 | F | 1-methyl-1H-tetrazol-5-yl | |
| 641 | pyridin-4-yl | CF3 | F | 1-methyl-1H-tetrazol-5-yl | |
| 642 | SCH2F | CF3 | I | imidazol-1-yl | |
| 643 | SCH2Cl | CF3 | I | imidazol-1-yl | |
| 644 | SCF3 | CF3 | I | imidazol-1-yl | |
| 645 | S(O)CH3 | CF3 | I | imidazol-1-yl | |
| 646 | S(O)CF3 | CF3 | I | imidazol-1-yl | |
| 647 | S(O)2CF3 | CF3 | I | imidazol-1-yl | |
| 648 | 6-phenylpyridin-4-yl | CF3 | I | imidazol-1-yl | |
| 649 | 6-phenylpyridin-4-yl | CF3 | I | imidazol-1-yl | |
| 650 | 6-chloropyridin-4-yl | CF3 | I | imidazol-1-yl | |
| 651 | 5-trifluoromethylpyridin-4-yl | CF3 | I | imidazol-1-yl | |
| 652 | 6-phenylpyridin-3-yl | CF3 | I | imidazol-1-yl | |
| 653 | 6-methylpyridin-3-yl | CF3 | I | imidazol-1-yl | |
| 654 | 6-chloropyridin-3-yl | CF3 | I | imidazol-1-yl | |
| 655 | 6-trifluoromethylpyridin-3-yl | CF3 | I | imidazol-1-yl | |
| 656 | pyridin-3-yl | CF3 | I | imidazol-1-yl | |
| 657 | 6-chloropyridin-2-yl | CF3 | I | imidazol-1-yl | |
| 658 | 6-trifluoromethylpyridin-2-yl | CF3 | I | imidazol-1-yl | |
| 659 | 3-methylpyrazol-1-yl | CF3 | I | imidazol-1-yl | |
| 660 | 3-methoxypyrazol-1-yl | CF3 | I | imidazol-1-yl | |
| 661 | 3-chloropyrazol-1-yl | CF3 | I | imidazol-1-yl | |
| 662 | 2-tolyl | CF3 | I | imidazol-1-yl | |
| 663 | 3-tolyl | CF3 | I | imidazol-1-yl | |
| 664 | 4-tolyl | CF3 | I | imidazol-1-yl | |
| 665 | 2-chlorophenyl | CF3 | I | imidazol-1-yl | |
| 666 | 3-chlorophenyl | CF3 | I | imidazol-1-yl | |
| 667 | 4-chlorophenyl | CF3 | I | imidazol-1-yl | |
| 668 | 2-methoxyphenyl | CF3 | I | imidazol-1-yl | |
| 669 | 3-methoxyphenyl | CF3 | I | imidazol-1-yl | |
| 670 | 4-methoxyphenyl | CF3 | I | imidazol-1-yl | |
| 671 | 2-(trifluoromethyl)phenyl | CF3 | I | imidazol-1-yl | |
| 672 | 3-(trifluoromethyl)phenyl | CF3 | I | imidazol-1-yl | |
| 673 | 4-(trifluoromethyl)phenyl | CF3 | I | imidazol-1-yl | |
| 674 | OCH2CF3 | CF3 | I | imidazol-1-yl | |

TABLE 1-continued

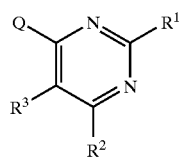

| No. | R1 | R2 | R3 | Q | mp (° C.) |
|---|---|---|---|---|---|
| 675 | OCH2C°CCH2Cl | CF3 | I | imidazol-1-yl | |
| 676 | OCH=CHCF3 | CF3 | I | imidazol-1-yl | |
| 677 | 4-methylimidazol-1-yl | CF3 | I | imidazol-1-yl | |
| 678 | 4-methoxyimidazol-1-yl | CF3 | I | imidazol-1-yl | |
| 679 | 4-chloroimidazol-1-yl | CF3 | I | imidazol-1-yl | |
| 680 | C°CCH2Cl | CF3 | I | imidazol-1-yl | |
| 681 | CF3 | CF3 | I | 1,2,4-triazol-1-yl | 137–138 |
| 682 | CF3 | CF2CF3 | I | 1,2,4-triazol-1-yl | |
| 683 | CF3 | CF3 | I | 2H-tetrazol-5-yl | |
| 684 | CF3 | CF2CF3 | I | 2H-tetrazol-5-yl | |
| 685 | CF3 | CF3 | I | 2-methyl-2H-tetrazol-5-yl | |
| 686 | CF3 | CF2CF3 | I | 2-methyl-2H-tetrazol-5-yl | |
| 687 | CF3 | CF3 | I | 4-methylimidazol-1-yl | |
| 688 | CF3 | CF2CF3 | I | 4-methylimidazol-1-yl | |
| 689 | CF3 | CF3 | I | benzimidazol-1-yl | |
| 690 | CF3 | CF2CF3 | I | benzimidazol-1-yl | |
| 691 | CF3 | CF2CF3 | I | imidazol-1-yl | |
| 692 | CF3 | CF3 | I | imidazol-1-yl | 105–106 |
| 693 | CF3 | CF3 | I | 2H-tetrazol-5-yl | |
| 694 | CF3 | CF3 | I | 2-methyl-2H-tetrazol-5-yl | |
| 695 | CF3 | CF3 | I | 2H-tetrazol-5-yl | |
| 696 | CF3 | CF3 | I | 2-methyl-2H-tetrazol-5-yl | |
| 697 | CF3 | CF3 | I | 2H-tetrazol-5-yl | |
| 698 | CF3 | CF3 | I | 2-methyl-2H-tetrazol-5-yl | |
| 699 | CH=CHCH2Cl | CF3 | I | imidazol-1-yl | |

What is claimed is:

1. A pyrimidine compound represented by the formula (1),

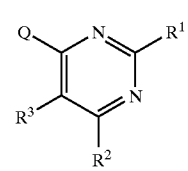

wherein $R^1$ is H, $C_1$–$C_6$alkyl (being optionally substituted by one or more of halogen), $C_2$–$C_6$alkenyl (being optionally substituted by one or more of halogen), $C_2$–$C_6$alkynyl (being optionally substituted by one or more of halogen or trialkylsilyl), $C_1$–$C_6$alkoxy (being optionally substituted by one or more of halogen), $C_2$–$C_6$alkenyloxy (being optionally substituted by one or more of halogen), $C_1$–$C_6$alkynyloxy (being optionally substituted by one or more of halogen), $C_1$–$C_6$alkylthio (being optionally substituted by one or more of halogen), $C_1$–$C_6$alkylsulfinyl (being optionally substituted by one or more of halogen), $C_1$–$C_6$alkylsulfonyl (being optionally substituted by one or more of halogen), phenyl (being optionally substituted by one or more of halogen, alkyl, haloalkyl or alkoxy), pyridin-2-yl (being optionally substituted by one or more of halogen, alkyl, haloalkyl or phenyl), pyridin-3-yl (being optionally substituted by one or more of halogen, alkyl, haloalkyl or phenyl), pyridin-4-yl (being optionally substituted by one or more of halogen, alkyl, haloalkyl or phenyl), imidazol-1-yl (being optionally substituted by one or more of halogen, alkyl or alkoxy), pyrazol-1-yl (being optionally substituted by one or more of halogen, alkyl or alkoxy) or $N(R^4)C(O)R^5$, $R^2$ is polyfluoro$C_1$–$C_6$alkyl, $R^3$ is fluorine, chlorine, bromine or iodine; ethenyl or ethynyl (being optionally substituted by one or more of halogen), $R^4$ and $R^5$ are, independently, H, $C_1$–$C_6$alkyl (being optionally substituted by one or more of halogen); or $R^4$ and $R^5$ can join together to form a 5 or 6 membered ring, Q is a heteroaromatic ring selected from the following ring system; imidazol-1-yl, pyrazol-1-yl, 1,2,3-triazol-1-yl, 1,2,3-triazol-2-yl, 1,2,4-triazol-1-yl, 1,2,4-triazol-4-yl, benzimidazol-1-yl or tetrazol-5-yl groups (being optionally substituted by one or more of halogen, cyano, hydroxy, mercapto, alkyl, haloalkyl, alkoxy, alkoxycarbonyl, amino, alkylamino, haloalkoxy, alkylthio or aralkylthio).

2. A fungicide for agricultural and horticultural use, comprising one or more of pyrimidine compounds represented by the formula (1)

wherein $R^1$ is H, $C_1$–$C_6$alkyl (being optionally substituted by one or more of halogen), $C_2$–$C_6$alkenyl (being optionally substituted by one or more of halogen), $C_2$–$C_6$alkynyl (being optionally substituted by one or more of halogen or trialkylsilyl), $C_1$–$C_6$alkoxy (being optionally substituted by one or more of halogen), $C_2$–$C_6$alkenyloxy (being optionally substituted by one or more of halogen), $C_1$–$C_6$alkynyloxy (being optionally substituted by one or more of halogen), $C_1$–$C_6$alkylthio (being optionally substituted by one or more of halogen), $C_1$–$C_6$alkylsulfinyl (being optionally substituted by one or more of halogen), $C_1$–$C_6$alkylsulfonyl (being optionally substituted by one or more of halogen), phenyl (being optionally substituted by one or more of halogen, alkyl, haloalkyl or alkoxy), pyridin-2-yl (being optionally substituted by one or more of halogen, alkyl, haloalkyl or phenyl), pyridin-3-yl (being optionally substituted by one or more of halogen, alkyl, haloalkyl or phenyl), pyridin-4-yl (being optionally substituted by one or more of halogen, alkyl, haloalkyl or phenyl), imidazol-1-yl (being optionally substituted by one or more of halogen, alkyl or alkoxy), pyrazol-1-yl (being optionally substituted by one or more of halogen, alkyl or alkoxy) or $N(R^4)C(O)R^5$, $R^2$ is polyfluoro$C_1$–$C_6$alkyl, $R^3$ is fluorine, chlorine, bromine or iodine; ethenyl or ethynyl (being optionally substituted by one or more of halogen), $R^4$ and $R^5$ are, independently, H, $C_1$–$C_6$alkyl (being optionally substituted by one or more of halogen); or $R^4$ and $R^5$ can join together to form a 5 or 6 membered ring, Q is a heteroaromatic ring selected from the following ring system; imidazol-1-yl, pyrazol-1-yl, 1,2,3-triazol-1-yl, 1,2,3-triazol-2-yl, 1,2,4-triazol-1-yl, 1,2,4-triazol-4-yl, benzimidazol-1-yl or tetrazol-5-yl groups (being optionally substituted by one or more of halogen, cyano, hydroxy, mercapto, alkyl, haloalkyl, alkoxy, alkoxycarbonyl, amino, alkylamino, haloalkoxy, alkylthio or aralkylthio), as the active principle and carrier.

* * * * *

UNITED STATES PATENT AND TRADEMARK OFFICE
CERTIFICATE OF CORRECTION

PATENT NO.     : 6,818,631 B1
DATED          : November 16, 2004
INVENTOR(S)    : Yuki Nakagawa et al.

It is certified that error appears in the above-identified patent and that said Letters Patent is hereby corrected as shown below:

Title page,
Item [57], ABSTRACT,
Line 16, replace with -- 1,2,3-triazol-2-yl, 1,2,4-triazol-1-yl, 1,2,4-triazol-4-yl, --.

Column 1,
Line 56, replace "pyridinyl" with -- pyridin-4-yl --.
Line 59, replace "alkoxyl" with -- alkoxy), --.

Column 3,
Line 15, replace "6membered ring," with -- 6-membered ring, --.
Line 53, replace "4chloropyrimidines" with -- 4-chloropyrimidines --.
Line 54, replace "alkyl phenyl," with -- alkyl, phenyl, --.
Line 55, replace "14" with -- 1-4 --.

Column 4,
SCHEME 3, replace "formula chain (3-1)" with -- 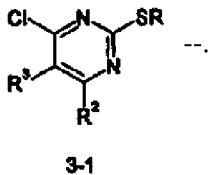 --.

Column 6,
Line 18, replace "4methoxypyrimidine" with -- 4-methoxypyrimidine --.
Line 56, replace "5-halogenooxypyrimidine" with -- 5-halogeno-4-methoxypyrimidine --.

Column 8,
Line 2, replace "tetrahydrofurwan," with -- tetrahydrofuran, --.

Column 10,
Line 36, replace "(Gloeosporium kala)" with -- (Gloeosporium kaki) --.

Column 13,
Line 49 replace "DMP" with -- DMF --.

Column 14,
Line 54, replace "5-Ethynyl-4-methoxy-2-methylt-6-" with -- 5-Ethynyl-4-methoxy-2-methyl-6- --.

UNITED STATES PATENT AND TRADEMARK OFFICE
CERTIFICATE OF CORRECTION

PATENT NO. : 6,818,631 B1
DATED : November 16, 2004
INVENTOR(S) : Yuki Nakagawa et al.

It is certified that error appears in the above-identified patent and that said Letters Patent is hereby corrected as shown below:

Column 15,
Line 31, replace "(hexanethyl acetate)." with -- (hexane-ethyl acetate). --.
Line 45 replace "TBF" with -- THF --.

Column 16,
Line 5, replace "6-trifluoromiethylpyrimidine" with -- 6-trifluoromethylpyrimidine --.
Line 9 under Example 11, replace "trifluoromehyl-pyrimidine" with
-- trifluoromethyl-pyrimidine --.
Line 23 under Example 12, replace "trifluoroethylpyrimidin-4-yl)-3-trifluoromethyl-lH-"
with -- trifluoromethylpyrimidin-4-yl)-3-trifluoromethyl-IH- --.
Line 24 under Example 12, replace "pyrazol-4-carboxylate" with -- pyrazole-4-carboxylate --.

Column 17,
Line 34, replace "5-Iodo-2-methylthio-4-(2H-tetrazol-5-yl)trifluoromethyl-" with
-- 5-Iodo-2-methylthio-4-(2H-tetrazol-5-yl)-6-trifluoromethyl- --.

Column 19,
Line 26, replace "class 11" with -- class II --.

Column 39,
Table 1-continued, No. 649 under heading R1 replace "6-phenylpyridin-4-yl" with
-- 6-methylpyridin-4-yl --.

Column 41,
Table 1-continued, No. 693 under heading R3 replace "I" with -- F --.
Table 1-continued, No. 694 under heading R3 replace "I" with -- F --.
Table 1-continued, No. 695 under heading R3 replace "I" with -- Cl --.
Table 1-continued, No. 696 under heading R3 replace "I" with -- Cl --.
Table 1-continued, No. 697 under heading R3 replace "I" with -- Br --.
Table 1-continued, No. 698 under heading R3 replace "I" with -- Br --.
Line 53, replace "$C_1$-$C_6$alkynyloxy" with -- $C_2$-$C_6$alkynyloxy --.

Column 42,
Line 45, replace "6 membered" with -- 6-membered --.

Column 43,
Line 6, replace "$C_1$-$C_6$alkynyloxy" with -- $C_2$-$C_6$alkynyloxy --.

UNITED STATES PATENT AND TRADEMARK OFFICE
CERTIFICATE OF CORRECTION

PATENT NO. : 6,818,631 B1
DATED : November 16, 2004
INVENTOR(S) : Yuki Nakagawa et al.

It is certified that error appears in the above-identified patent and that said Letters Patent is hereby corrected as shown below:

<u>Column 44,</u>
Line 9, replace "6 membered" with -- 6-membered --.

Signed and Sealed this

Fifteenth Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,818,631 B1 Page 1 of 1
DATED : November 16, 2004
INVENTOR(S) : Yuki Nakagawa et al.

It is certified that error appears in the above-identified patent and that said Letters Patent is hereby corrected as shown below:

Column 39,
Table 1-continued, No. 651 under heading R1 replace
"5-trifluoromethylpyridin-4-yl" with -- 6-trifluoromethylpyridin-4-yl --

Signed and Sealed this

Third Day of May, 2005

JON W. DUDAS
*Director of the United States Patent and Trademark Office*